(12) United States Patent
Keil et al.

(10) Patent No.: US 11,839,505 B2
(45) Date of Patent: Dec. 12, 2023

(54) MEDICAL IMAGING DEVICE AND METHOD OF OPERATING A MEDICAL IMAGING DEVICE

(71) Applicant: HOLOGIC, INC., Marlborough, MA (US)

(72) Inventors: Richard Keil, Charlestown, MA (US); Daniel Santos, Westborough, MA (US); Mark Guetersloh, Bedford, MA (US); Kevin Wilson, Acton, MA (US); Tri Pham, Arlington, MA (US); Aleksey Danilkin, Maynard, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/479,767

(22) Filed: Sep. 20, 2021

(65) Prior Publication Data

US 2022/0071579 A1 Mar. 10, 2022

Related U.S. Application Data

(63) Continuation of application No. 16/347,577, filed as application No. PCT/US2017/059807 on Nov. 2, 2017, now Pat. No. 11,147,525.
(Continued)

(51) Int. Cl.
*A61B 6/00* (2006.01)

(52) U.S. Cl.
CPC ............. *A61B 6/4441* (2013.01); *A61B 6/44* (2013.01); *A61B 6/4411* (2013.01); *A61B 6/4429* (2013.01); *A61B 6/4435* (2013.01); *A61B 6/4452* (2013.01); *A61B 6/4458* (2013.01); *A61B 6/4476* (2013.01); *A61B 6/46* (2013.01); *A61B 6/54* (2013.01); *A61B 6/542* (2013.01); *A61B 6/544* (2013.01); *A61B 6/545* (2013.01);
(Continued)

(58) Field of Classification Search
CPC ....... A61B 6/44; A61B 6/4405; A61B 6/4411; A61B 6/4429; A61B 6/4435; A61B 6/4441; A61B 6/4447; A61B 6/4452; A61B 6/4476; A61B 6/46; A61B 6/467; A61B 6/58; A61B 6/587; A61B 6/588
USPC .................. 378/62, 196–198, 189, 205–207
See application file for complete search history.

(56) References Cited

U.S. PATENT DOCUMENTS 5,666,392 A 9/1997 Ploetz
6,213,638 B1 4/2001 Rattner
(Continued)

FOREIGN PATENT DOCUMENTS

CN 1571648 1/2005
CN 101623200 A 1/2010
(Continued)

OTHER PUBLICATIONS

PCT International Search Report on Patentability in International Patent Application No. PCT/US2017/059807, dated Feb. 8, 2018, 14 pages.
(Continued)

*Primary Examiner* — Allen C. Ho
(74) *Attorney, Agent, or Firm* — Merchant & Gould P.C.

(57) ABSTRACT

A medical imaging device includes an x-ray source disposed at a first end of an arm, and an x-ray detector disposed at a second end of the arm opposite of the x-ray source. At least one of the x-ray source, the x-ray detector, and a portion of the arm are selectively adjustable with respect to the arm.

20 Claims, 17 Drawing Sheets

Related U.S. Application Data

(60) Provisional application No. 62/417,588, filed on Nov. 4, 2016.

(52) U.S. Cl.
CPC ............... *A61B 6/58* (2013.01); *A61B 6/587* (2013.01); *A61B 6/588* (2013.01); *A61B 6/4405* (2013.01); *A61B 6/467* (2013.01)

(56) References Cited

U.S. PATENT DOCUMENTS

| | | | |
|---|---|---|---|
| 6,282,264 B1 | 8/2001 | Smith et al. | |
| 6,325,537 B1 | 12/2001 | Watanabe | |
| 6,412,978 B1 | 7/2002 | Watanabe | |
| 6,428,206 B1 | 8/2002 | Watanabe | |
| 6,496,558 B2 | 12/2002 | Graumann | |
| 6,619,840 B2 | 9/2003 | Rasche | |
| 6,859,521 B2* | 2/2005 | Spahn | A61B 6/08 378/197 |
| 6,869,217 B2 | 3/2005 | Rasche | |
| 6,872,000 B2 | 3/2005 | Atzinger | |
| 6,940,941 B2* | 9/2005 | Gregerson | A61B 6/4411 378/197 |
| 7,108,421 B2 | 9/2006 | Gregerson | |
| 7,300,205 B2* | 11/2007 | Grady | A61B 6/504 378/197 |
| 7,515,677 B2 | 4/2009 | Zellerhoff | |
| 7,530,739 B2* | 5/2009 | Lurz | A61B 6/4441 378/197 |
| 7,585,110 B2* | 9/2009 | Timmermans | A61B 6/4441 378/197 |
| 7,591,589 B2* | 9/2009 | Grebner | A61B 6/4441 378/197 |
| 7,614,786 B2 | 11/2009 | Baumann | |
| 7,664,222 B2* | 2/2010 | Jabri | A61B 6/547 378/26 |
| 7,711,083 B2 | 5/2010 | Heigl | |
| 7,748,900 B2* | 7/2010 | Maschke | A61B 6/4458 378/197 |
| 7,806,589 B2 | 10/2010 | Tashman | |
| 7,835,490 B2* | 11/2010 | Ramsauer | A61B 90/14 378/197 |
| 7,837,385 B2 | 11/2010 | Klingenbeck-Regn | |
| 7,942,575 B2* | 5/2011 | Fehre | A61B 6/4429 378/197 |
| 7,988,357 B2* | 8/2011 | Hornung | A61B 6/4458 378/197 |
| 8,136,989 B2* | 3/2012 | Atzinger | A61B 6/4476 378/204 |
| 8,297,839 B2* | 10/2012 | Tsujii | A61B 6/4441 378/197 |
| 8,303,181 B2* | 11/2012 | Sukovic | A61B 6/547 378/197 |
| 8,320,517 B2* | 11/2012 | Dennerlein | A61B 6/587 378/4 |
| 8,348,506 B2 | 1/2013 | Yorkston | |
| 8,451,972 B2* | 5/2013 | Dafni | A61B 6/06 378/11 |
| 8,534,915 B2* | 9/2013 | Maschke | A61B 6/4458 378/197 |
| 8,767,920 B2 | 7/2014 | Spahn | |
| 9,039,282 B2* | 5/2015 | Maschke | A61B 6/4458 378/197 |
| 9,176,077 B2 | 11/2015 | Ikawa | |
| 9,554,761 B2* | 1/2017 | Baumann | A61B 6/4441 |
| 9,625,581 B2 | 4/2017 | Chang | |
| 9,655,568 B2 | 5/2017 | Ritschl | |
| 9,717,467 B2* | 8/2017 | Litzenberger | A61B 6/541 |
| 9,737,275 B2* | 8/2017 | Noda | A61B 6/0407 |
| 9,782,139 B2* | 10/2017 | Barth | A61B 6/4429 |
| 9,795,347 B2* | 10/2017 | Jan | A61B 6/025 |
| 9,801,598 B2* | 10/2017 | Zaiki | A61B 6/4441 |
| 9,855,015 B2* | 1/2018 | Risher-Kelly | A61B 6/4405 |
| 9,855,016 B2* | 1/2018 | Lee | A61B 6/4464 |
| 9,855,446 B2 | 1/2018 | Chang | |
| 9,895,559 B2 | 2/2018 | Chang | |
| 9,949,703 B2 | 4/2018 | Dirisio | |
| 9,962,133 B2* | 5/2018 | Risher-Kelly | A61B 6/4441 |
| 10,028,713 B2* | 7/2018 | Risher-Kelly | A61B 6/4447 |
| 10,071,265 B2 | 9/2018 | Chang | |
| 10,076,302 B2* | 9/2018 | Franklin | A61B 6/4417 |
| 10,154,824 B2* | 12/2018 | Fortuna | A61B 6/547 |
| 10,213,171 B2 | 2/2019 | Masuo | |
| 10,448,910 B2* | 10/2019 | Johnson | A61B 6/032 |
| 10,478,135 B2 | 11/2019 | Kuspert | |
| 10,548,540 B2 | 2/2020 | Dirisio | |
| 10,779,780 B2* | 9/2020 | Agrahari | A61B 6/4482 |
| 10,993,685 B2* | 5/2021 | Schraven | A61B 6/4441 |
| 11,147,525 B2* | 10/2021 | Keil | A61B 6/542 |
| 2003/0112926 A1 | 6/2003 | Atzinger | |
| 2007/0183587 A1 | 8/2007 | Baumann et al. | |
| 2008/0198973 A1 | 8/2008 | Timmermans et al. | |
| 2010/0303207 A1 | 12/2010 | Tsuji et al. | |
| 2011/0170660 A1 | 7/2011 | Atzinger et al. | |
| 2012/0014512 A1 | 1/2012 | Kim et al. | |
| 2012/0213332 A1 | 8/2012 | Dirauf et al. | |
| 2013/0182829 A1 | 7/2013 | Nguyen et al. | |
| 2014/0037058 A1 | 2/2014 | Allen et al. | |
| 2018/0070910 A1 | 3/2018 | Franklin et al. | |

FOREIGN PATENT DOCUMENTS

| | | |
|---|---|---|
| CN | 102196772 | 9/2011 |
| CN | 103654813 A | 3/2014 |
| CN | 104684483 A | 6/2015 |
| JP | H0524005 U | 3/1993 |
| WO | 9933116 A1 | 7/1999 |
| WO | 2007029202 A2 | 3/2007 |

OTHER PUBLICATIONS

PCT International Preliminary Report and Written Opinion for the International Patent Application No. PCT/US2017/059807, dated May 16, 2019, 9 pages.

\* cited by examiner

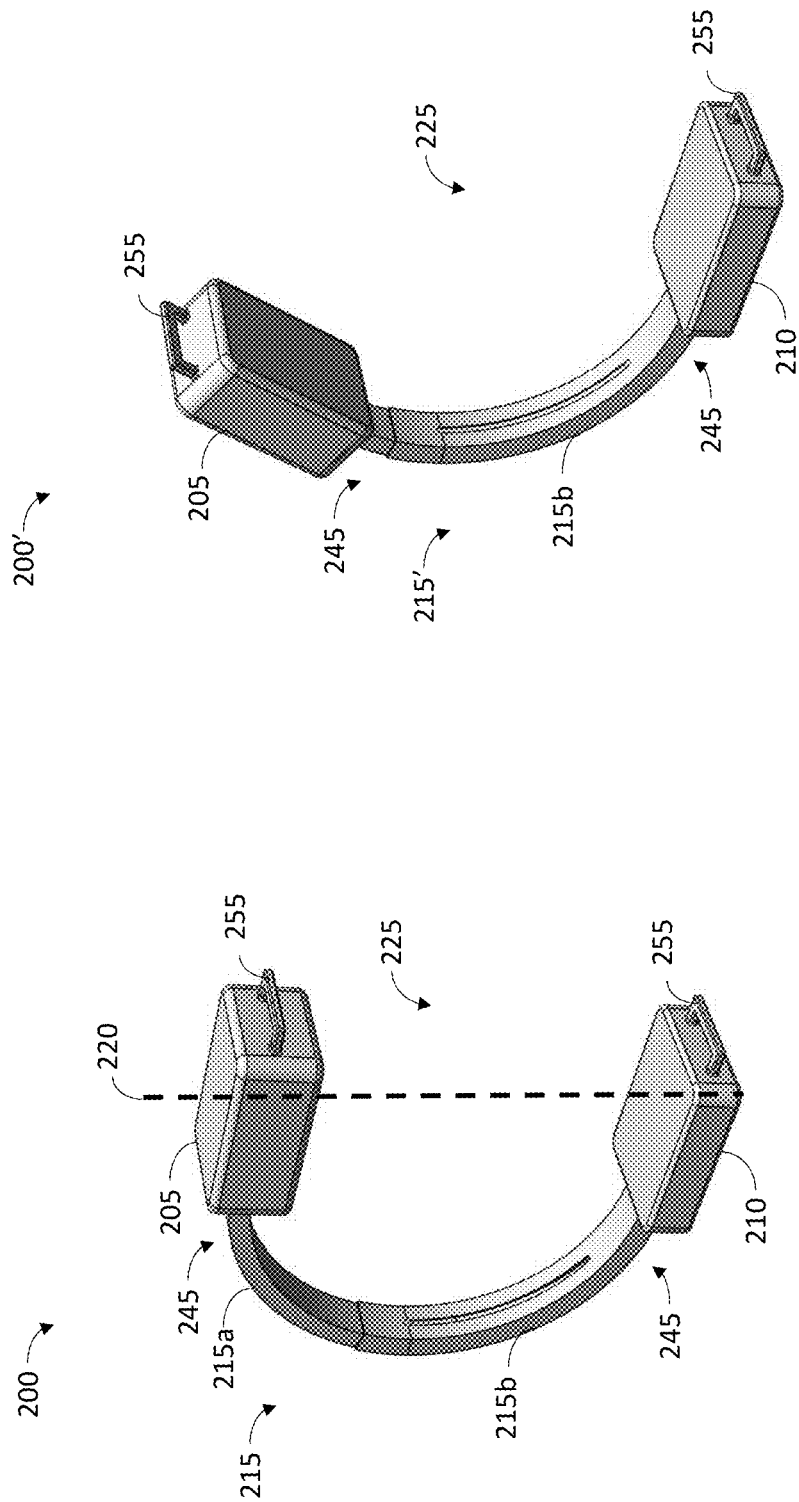

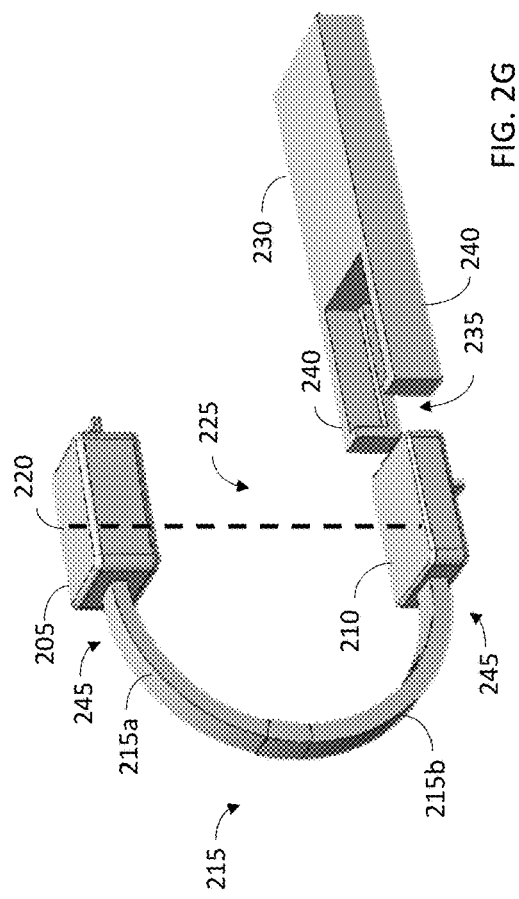

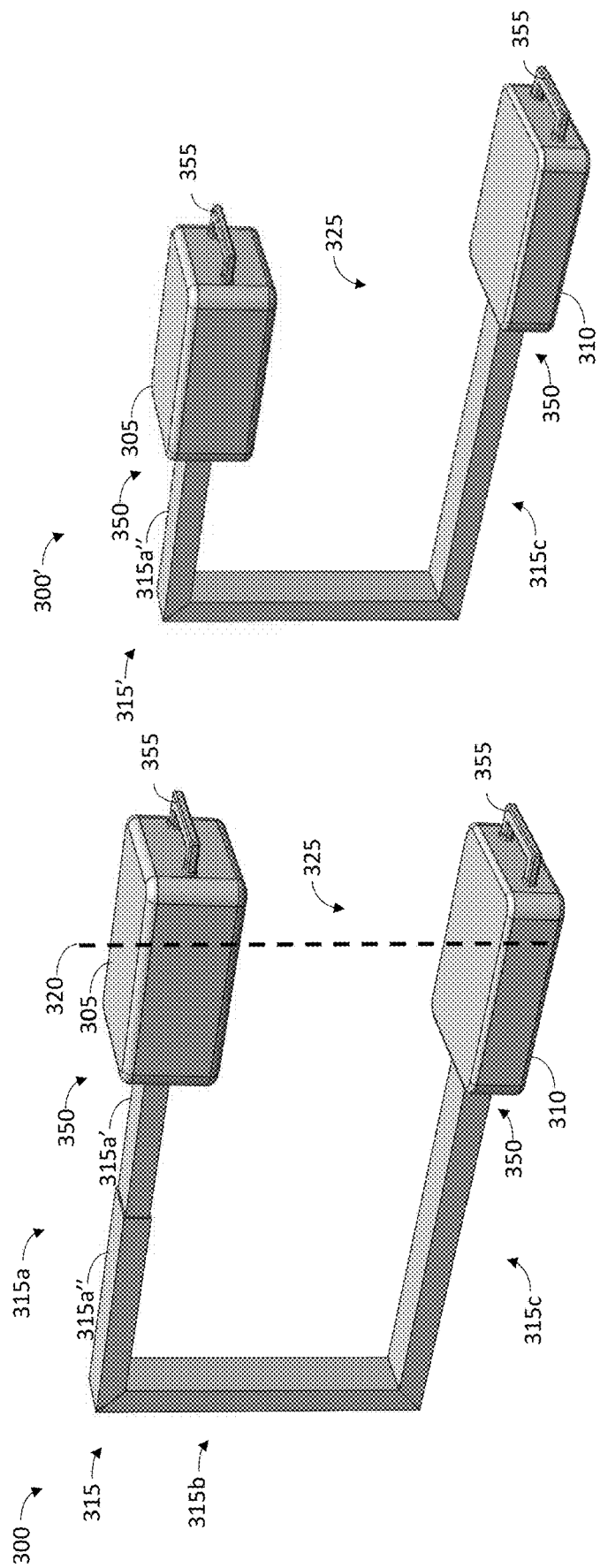

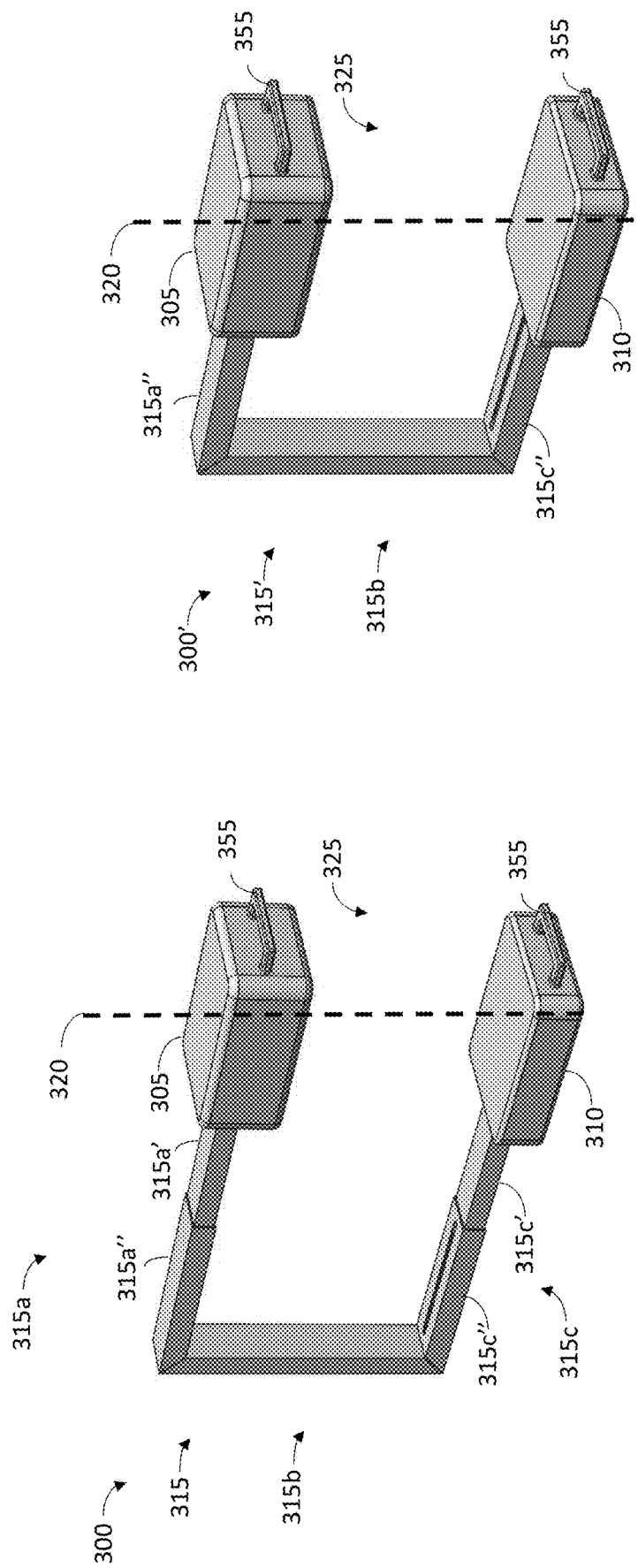

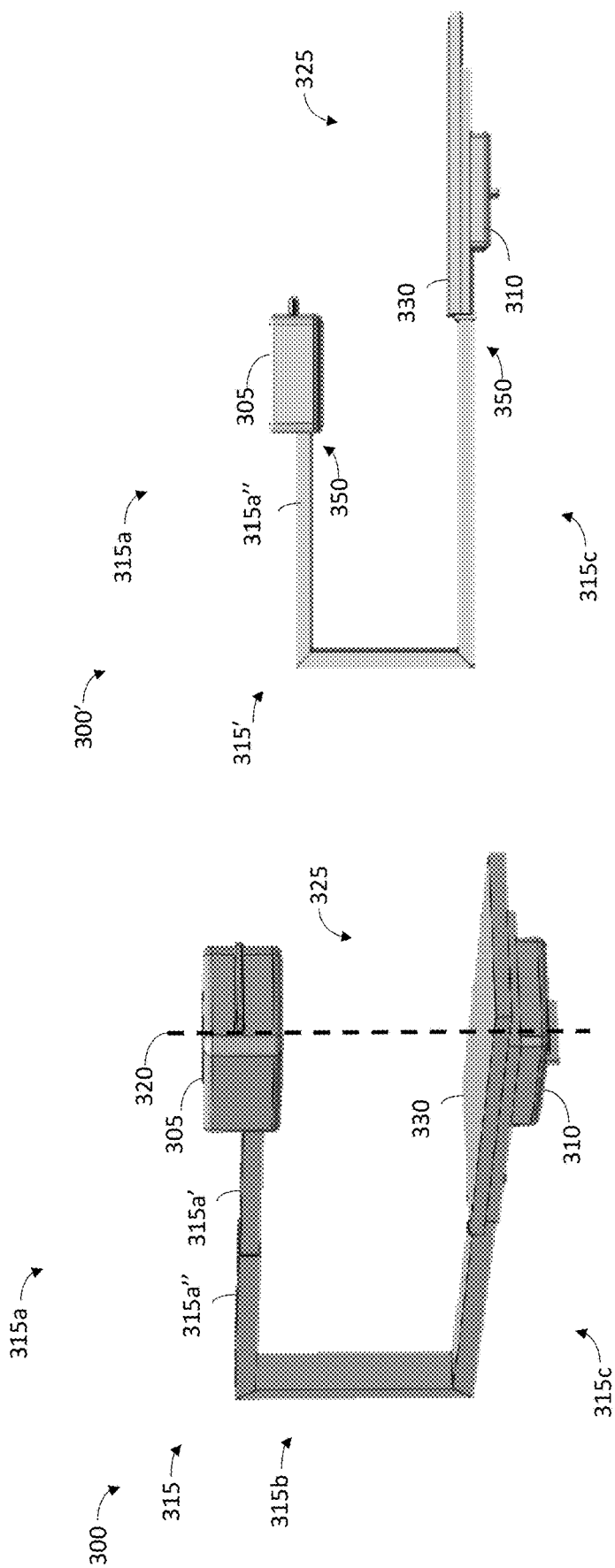

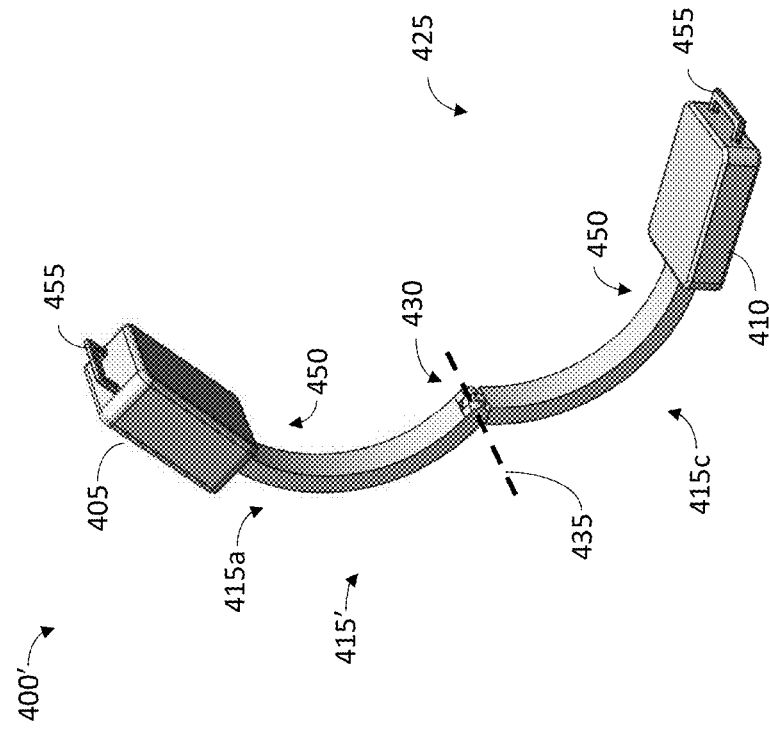
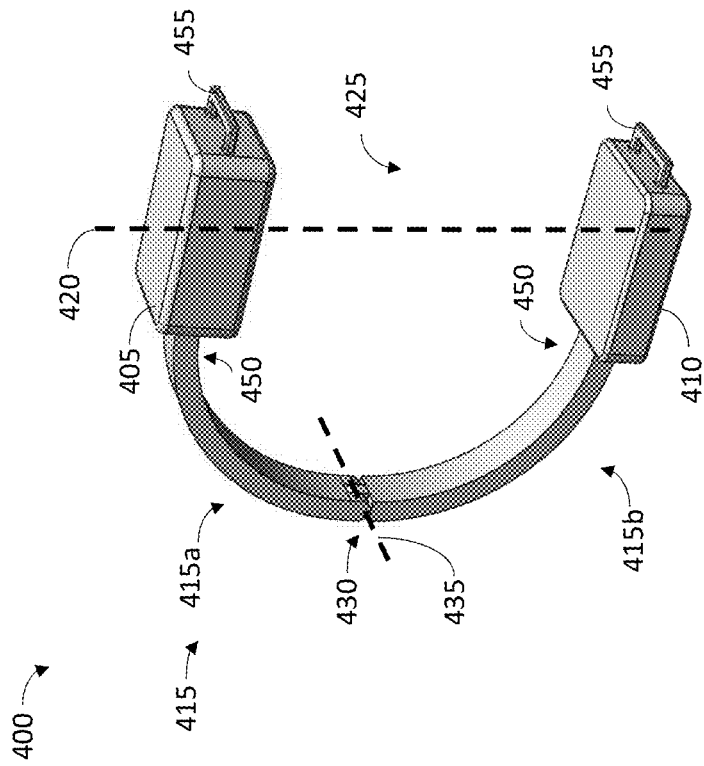
FIG. 4B
FIG. 4A

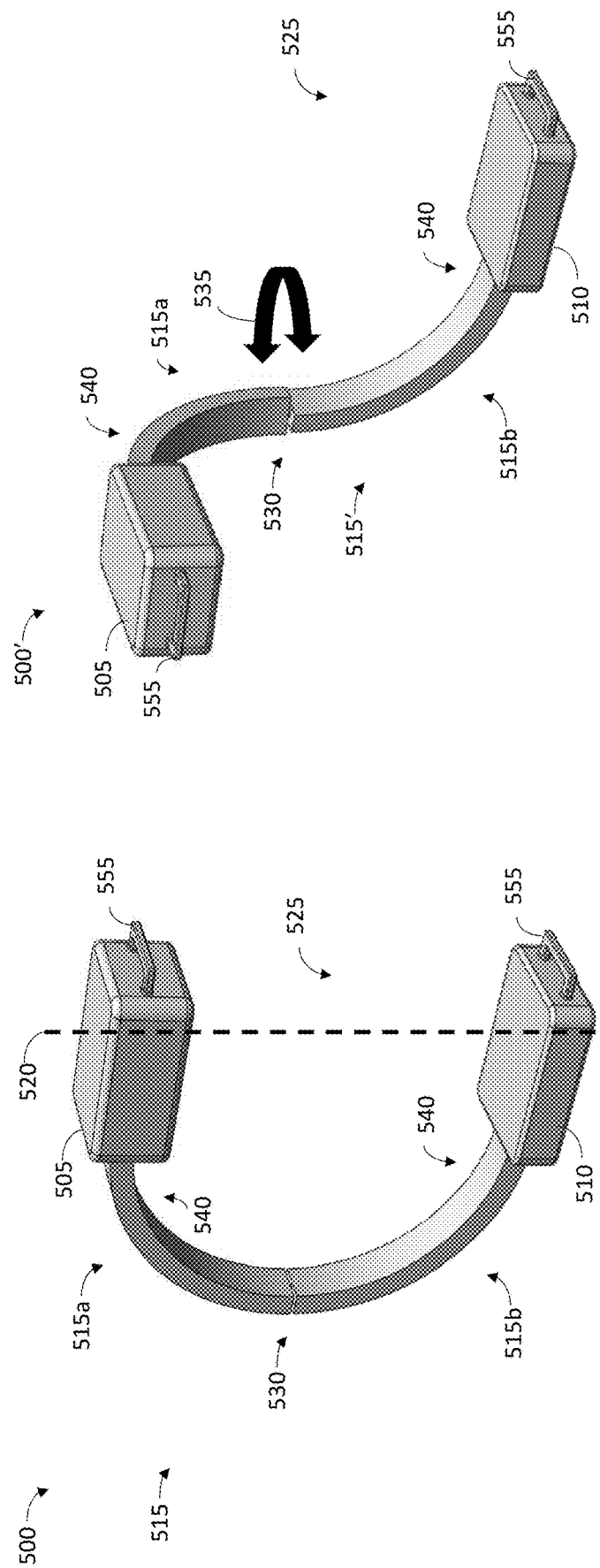

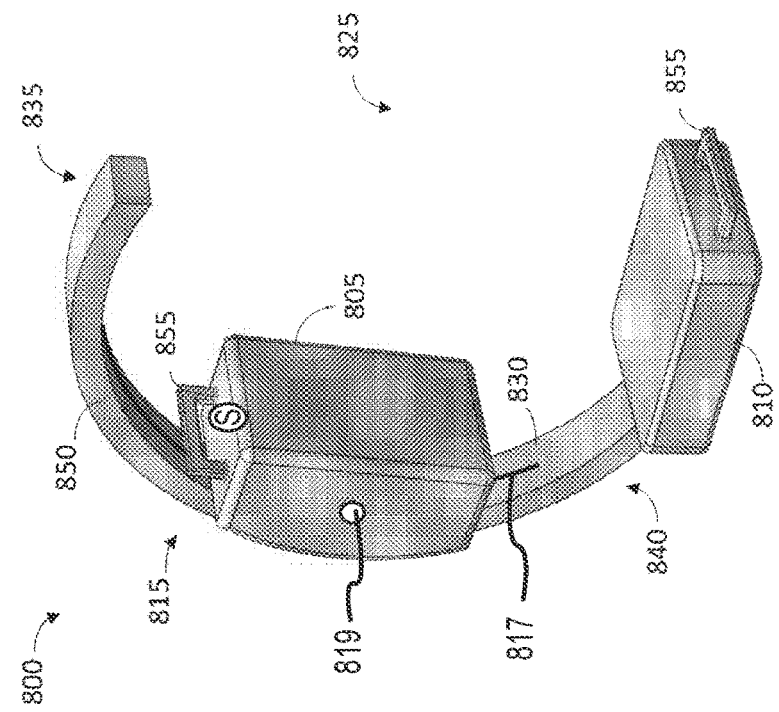
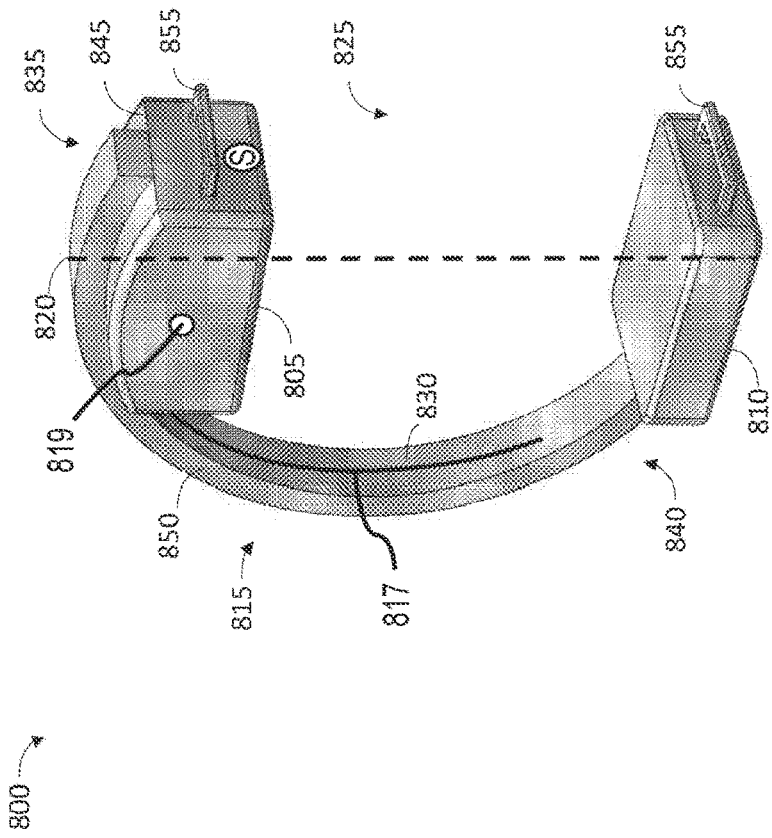
FIG. 8B
FIG. 8A

MEDICAL IMAGING DEVICE AND METHOD OF OPERATING A MEDICAL IMAGING DEVICE

CROSS-REFERENCE TO RELATED APPLICATIONS

This application is a Continuation of U.S. patent application Ser. No. 16/347,577, filed on May 4, 2019, now U.S. Pat. No. 11,147,525, which is a U.S. National Phase of International Patent Application No. PCT/US2017/059807, filed on Nov. 2, 2017, which claims the benefit of U.S. Provisional Patent Application Ser. No. 62/417,588, filed on Nov. 4, 2016. The contents of U.S. patent application Ser. No. 16/347,577, International Patent Application No. PCT/US2017/059807, and U.S. Provisional Patent Application Ser. No. 62/417,588 are hereby incorporated herein by reference in their respective entireties for all purposes.

FIELD OF THE DISCLOSURE

The disclosure generally relates to a medical imaging device, and more particularly to the configuration and operation of the fluoroscopy imaging device.

BACKGROUND OF THE INVENTION

Known fluoroscopic imaging devices take x-ray images of bone and tissue of a patient and displays an optical image of the x-ray on a monitor. Such devices can be used in medical environments such as operating rooms and clinics for on-site imaging and analysis during a surgical procedure. Such devices may include a portable cabinet having a power supply, controller, memory, processor, display screen, and/or user interface operably connected to each other for operating the fluoroscopic imaging device. Attached to and extending from the cabinet is typically a C-arm having an x-ray source and an x-ray detector coupled at opposite ends of the C-arm. While the C-arm may be manipulated with respect to the cabinet, the x-ray source and the x-ray detector are typically fixed relative to their positions on the C-arm.

Imaging of a patient is often done prior to, and/or at various times throughout, a surgical procedure with the use of an x-ray device that includes a C-arm. When an image is taken, the C-arm may be moved into position around the patient or the patient's extremity. When imaging is complete, the C-arm must then be fully moved away from the patient so that a medical profession may access the patient to perform the surgical procedure. During or at the conclusion of the surgical procedure, another image may be necessary to verify bone settings and/or implants, e.g., screws, plates, and/or rods. The C-arm must then be moved back into position around the patient so that the image may be captured. Moving the C-arm can be difficult and cumbersome in confined operating rooms. Additionally, adjusting the device into a position for imaging, moving it away from the patient to perform a surgical procedure, and then bringing it back into position for imaging is time consuming and extends unnecessarily the length of a surgical procedure of the patient.

It is with respect to these and other considerations that the present inventions may be useful.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one aspect, the present invention comprises a medical imaging device, comprising an x-ray source disposed at a first end of an arm and an x-ray detector disposed at a second end of the arm opposite of the x-ray source. At least one of the x-ray source, the x-ray detector, and at least a portion of the arm are selectively adjustable with respect to the arm.

In another aspect, the present invention comprises a medical imaging device, comprising an arm, an x-ray source rotatably connected to a first end of the arm, and an x-ray detector rotatably connected to a second end of the arm. At least one of the x-ray source, the x-ray detector, and a portion of the arm are selectively adjustable with respect to the arm.

In another aspect, the present invention comprises a medical imaging device, comprising an x-ray source and an x-ray detector, wherein the x-ray source and the x-ray detector are independent of each other and at least one of the x-ray source and the x-ray detector are selectively adjustable.

In another aspect, the present invention comprises a medical imaging device, comprising a base cabinet, and an arm coupled to the base cabinet. The arm includes an x-ray source and an x-ray detector disposed at opposing ends of the arm, and the x-ray source, the x-ray detector, and a portion of the arm are selectively adjustable with respect to the arm.

In yet another aspect, the present invention comprises a method of operating a medical imaging device, comprising aligning an x-ray source disposed at a first end of an arm and an x-ray detector disposed at a second end of the arm opposite the first end of the arm, wherein x-rays emitted from the x-ray source are receivable by the x-ray detector through a space between the first end of the arm and the second end of the arm; adjusting at least one of the x-ray source and the x-ray detector with respect to the arm, wherein the x-ray source and the x-ray detector are out of alignment from each other; accessing the space between the first end of the arm and the second end of the arm; and re-aligning the x-ray source and the x-ray detector.

BRIEF DESCRIPTION OF THE DRAWINGS

By way of example, a specific embodiment of the disclosed device will now be described, with reference to the accompanying drawings, in which:

FIGS. 2A-2B illustrate a perspective view of an arm of the medical imaging device according to an embodiment of the present invention.

FIGS. 2E-2G illustrate a perspective view of an arm of the medical imaging device according to another embodiment of the present invention.

FIGS. 3A-3B illustrate a perspective view of an arm of the medical imaging device according to another embodiment of the present invention.

FIGS. 3C-3D illustrate a perspective view of an arm of the medical imaging device according to another embodiment of the present invention.

FIGS. 3E-3H illustrate a perspective view of an arm of the medical imaging device according to another embodiment of the present invention.

FIGS. 4A-4B illustrate a perspective view of an arm of the medical imaging device according to another embodiment of the present invention.

FIGS. 5A-5B illustrate a perspective view of an arm of the medical imaging device according to another embodiment of the present invention.

FIGS. 8A-8B illustrate a perspective view of an arm of the medical imaging device according to another embodiment of the present invention.

DETAILED DESCRIPTION

Figure 1:
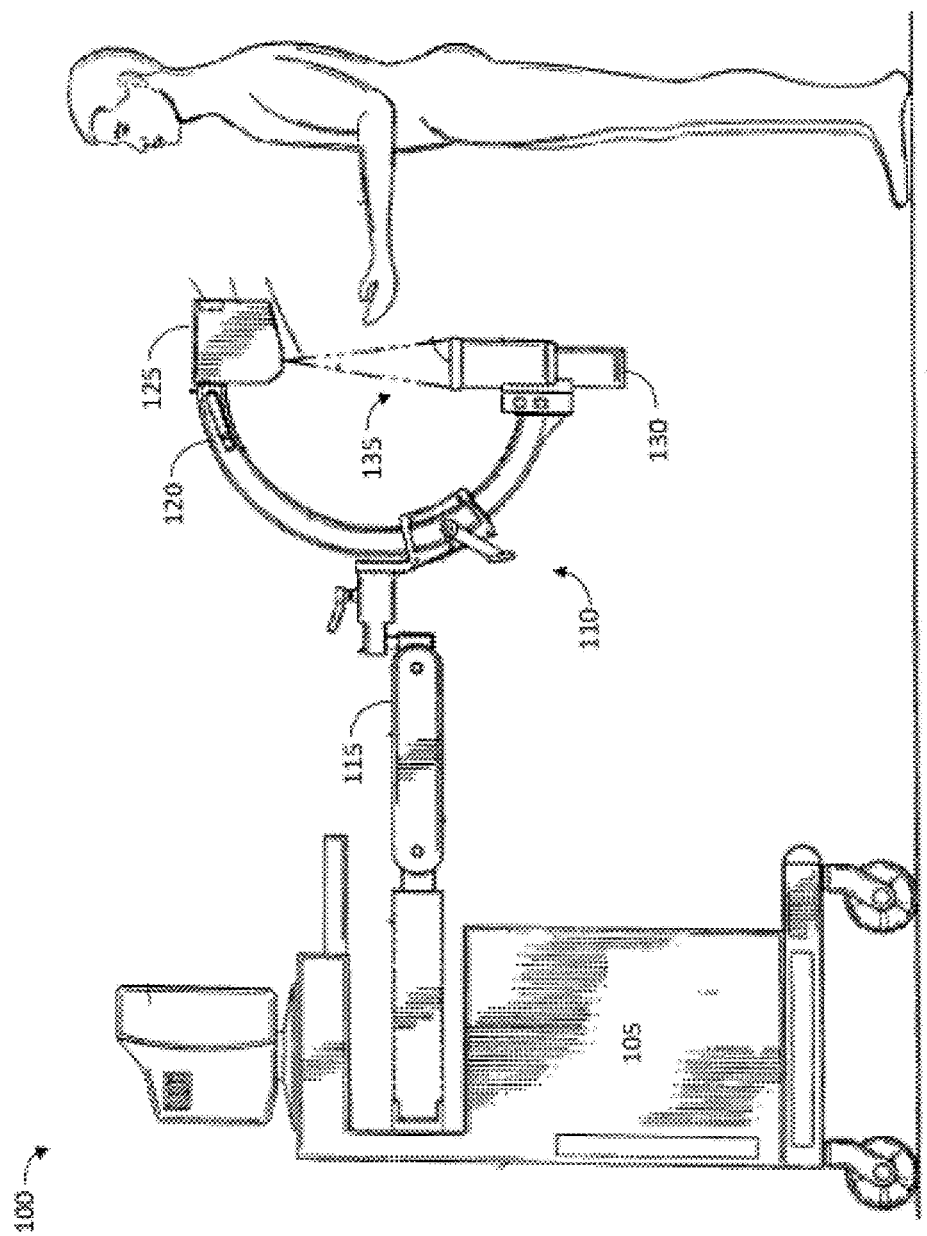
FIG. 1 illustrates a perspective view of an existing medical imaging device.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Referring to FIG. 1, a known medical imaging device 100 is shown. The medical imaging device 100 may include a cabinet 105, which may be portable, e.g., on wheels. The cabinet 105 may include a power supply, controller, memory, processor, display screen, and/or user interface (not shown) operably connected to each other for operating the medical imaging device 100. An arm assembly 110 may be connected to the cabinet 105, via an articulating arm 115. The arm assembly 110 may include a "C" shaped arm 120, having an x-ray source 125 disposed at one end of the "C" shaped arm 120 and an x-ray detector 130 disposed at the opposite end. A space 135 between the x-ray source 125 and the x-ray detector 130 is large enough to receive at least a portion of a patient for imaging, e.g., an arm, a hand, a leg, a foot, a torso, or a combination thereof. It should be understood that the use of "patient" throughout this description may include an extremity or part of an extremity of a patient. Also, it should be understood that a "C" shaped arm 120, as described with reference to various embodiments of the present invention, do not necessarily conform to the exact shape of a "C" and include any configuration that includes the arc of a circle, a portion of an oval, or other curvature(s) or angled portions that result in an x-ray source 125 being positioned opposite from (and at a distance from) an x-ray detector 130. While the arm assembly 110 may be rotatable relative to the cabinet 105 and/or the articulating arm 115, the arm assembly 110 is fixed. For example, the position of the x-ray source 125 relative to the x-ray detector 130 with respect to the "C" shaped arm 120 is fixed.

The arm assembly 110 may be positioned relative to a patient for scanning. When the scanning is completed, the entire arm assembly 110 must be moved away from the patient so a medical professional may access the scanned limb. Often, the arm assembly 110 must subsequently be moved back to the patient for additional scanning. For example, a medical professional may image a patient's limb prior to an operation. They may then perform surgery, for example, implanting screws, plates, and/or rods. Once the implant is complete, another image is taken to ensure proper placement of the implant. As described above, adjusting the arm assembly 110 multiple times for a single procedure is time consuming, and may introduce error in that the positioning may not be repeatable with respect to the patient. This results in images that are not entirely identical.

Figure 2D:
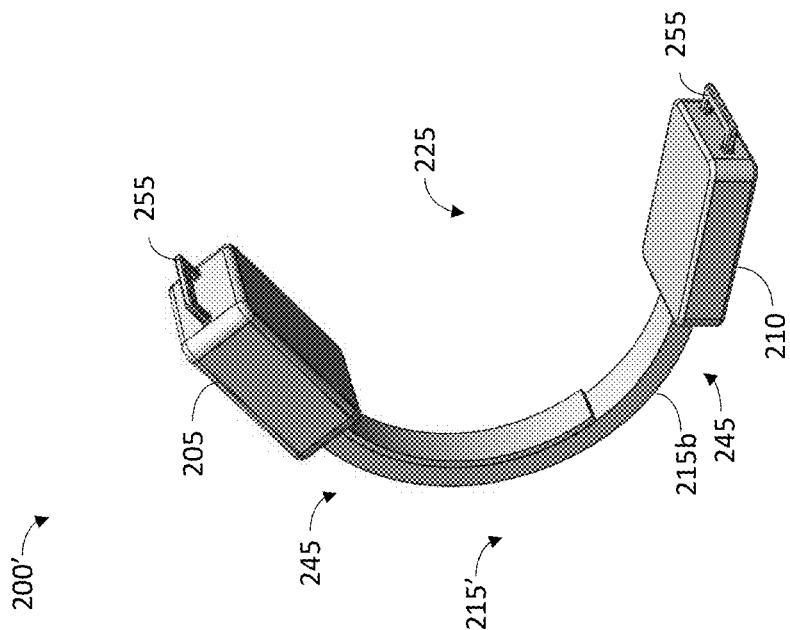
FIGS. 2C-2D illustrate a perspective view of an arm of the medical imaging device according to another embodiment of the present invention.

Referring now to FIGS. 2A-2G, various embodiments of an arm assembly 200, 200' according to the present invention are shown. FIG. 2A illustrates an arm assembly 200, including an x-ray source 205 coupled at an end 245 of an arm 215, and an x-ray detector 210 coupled at an opposite end 245 of the arm 215. The arm 215 may include a curvature, for example, in a general "C" shape, so that the x-ray source 205 and the x-ray detector 210 are aligned along an imaging axis 220 when disposed at the ends 245 of the arm 215. FIG. 2A illustrates the arm assembly 200 in a first arrangement in which the x-ray detector 210 is opposite of the x-ray source 205. FIG. 2B illustrates the arm assembly 200' in a second arrangement in which the x-ray source 205 and x-ray detector 210 are out of alignment with each other.

A space 225 may be created between the x-ray source 205 and the x-ray detector 210 by the alignment of the x-ray source 205 and the x-ray 210. A patient may be positioned within the space 225 so that an image may be taken. However, when the x-ray source 205 and the x-ray detector 210 are aligned, access to the space 225 may be limited. For example, a patient may be positioned in the space 225, but a surgical procedure cannot occur without moving at least one of the patient, the x-ray source 205, and/or the x-ray detector 210.

Figure 2C:
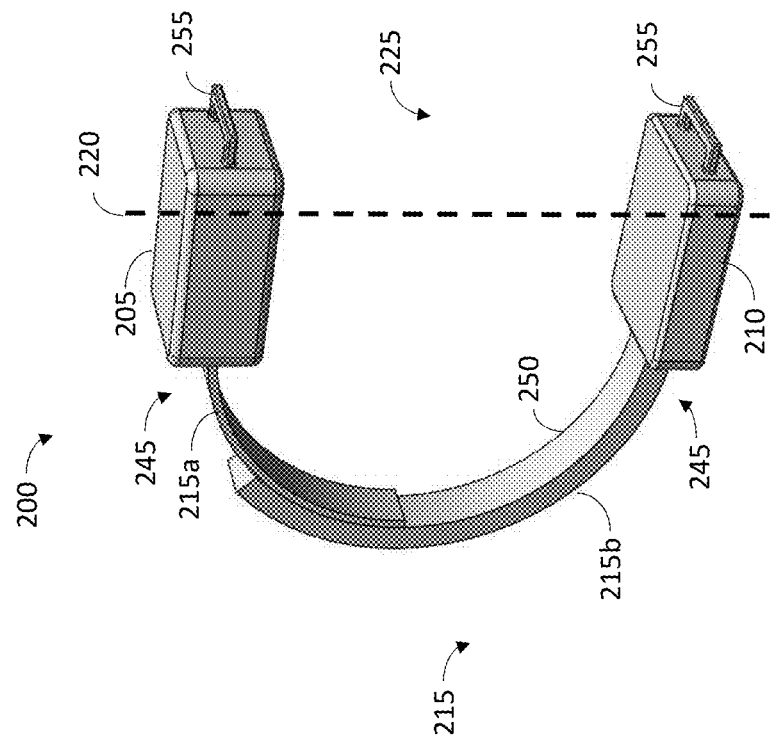

Referring to FIGS. 2C and 2D, FIG. 2C illustrates the arm assembly 200 in a first arrangement in which the x-ray detector 210 is opposite of the x-ray source 205. FIG. 2D illustrates the arm assembly 200' in a second arrangement in which the x-ray source 205 and x-ray detector 210 are out of alignment with each other. As illustrated, for the patient to remain stationary, the arm 215 may be retractable; for example, a first portion 215a may be slidable within a second portion 215b. As shown in FIG. 2B, the first portion 215a is positioned within the second portion 215b, showing a retracted arm 215'. The first portion 215a may be dimensioned smaller than the second portion 215b. The second portion 215b may be generally hollow in order to receive the first portion 215a. In an embodiment, the first portion 215a may be slidable along a second portion 215b. For example, the first portion 215a is repositioned along an exterior surface 250 of the arm 215. As shown in FIGS. 2C-2D, the first portion 215a is slidable along the second portion 215b, so that the x-ray source 205 is repositioned relative to the x-ray detector 210 in a similar manner as in FIGS. 2A-2B, described in detail below.

When the first portion 215a is adjusted relative to the second portion 215b, the position of the x-ray source 205 relative to the x-ray detector 210 is altered. This is advantageous over existing arm assemblies for imaging devices in that one end 245 of the arm 215 may remain stationary while the other end 245 of the arm 215 is repositioned. For example, a patient may be positioned relative to the x-ray detector 210 in the space 225 for imaging prior to a surgical procedure. Once the imaging is complete, the x-ray source 205 may be re-positioned by retracting the first portion 215*a* of the arm 215 into the second portion 215*b*. The x-ray detector 210 remains stationary relative to the patient. In an embodiment, the x-ray detector 210 is repositioned while the x-ray source 205 remains stationary relative to the patient. Regardless of whether one or both of the x-ray source 205 and the x-ray detector are repositioned relative to each other, they may be brought out of alignment with each other along imaging axis 220 to provide access to the space 225. When the x-ray source 205 is out of alignment from the x-ray detector 210, a medical professional has greater access to the patient in the space 225, e.g., to conduct the surgical procedure. Upon completion of the procedure, the arm 215 may be adjusted to the original position, e.g., the first portion 215*a* is extended out of the second portion 215*b*.

In an embodiment, one of the x-ray source 205 or the x-ray detector 210 may be attachable to a table 230, as shown in FIGS. 2E-2G. In an embodiment, the x-ray detector 210 is attachable to the table 230. The x-ray detector 210, when attached to the table 230, may form a portion of the table 230. For example, a cut-out 235 may be configured to receive the x-ray detector 210. Projections 240 may extend from the table 230, forming the cut-out 235, to attach and retain the x-ray detector 210. The projections 240 may form a shelf in the cut-out 235 for the x-ray source 205 and/or the x-ray detector 210 to slide into position with the table 230. FIG. 2E illustrates the arm assembly 200 in a first arrangement in which the x-ray detector 210 is opposite of the x-ray source 205. FIG. 2F illustrates the arm assembly 200' in a second arrangement in which the x-ray source 205 and x-ray detector 210 are out of alignment with each other.

In some embodiments, a patient may be positioned on the table 230 and the x-ray detector 210. The arm 215 may be positioned by sliding the x-ray detector 210 within the projections 240. The x-ray source 205 is thereby positioned relative to the patient on the table 230 and the x-ray detector 210, in the space 225. Including the x-ray detector 210 as a portion of the table 230 as shown in FIGS. 2E-2G is advantageous in facilitating ease of use of the imaging device in an operating room. For example, patient movement may be minimized for an entire medical procedure in that the combined table 230 and x-ray detector 210 is capable of imaging a patient as well as providing an operating surface. Time needed for the procedure is thereby reduced by eliminating unnecessary patient movement during the medical procedure.

Figure 3H:
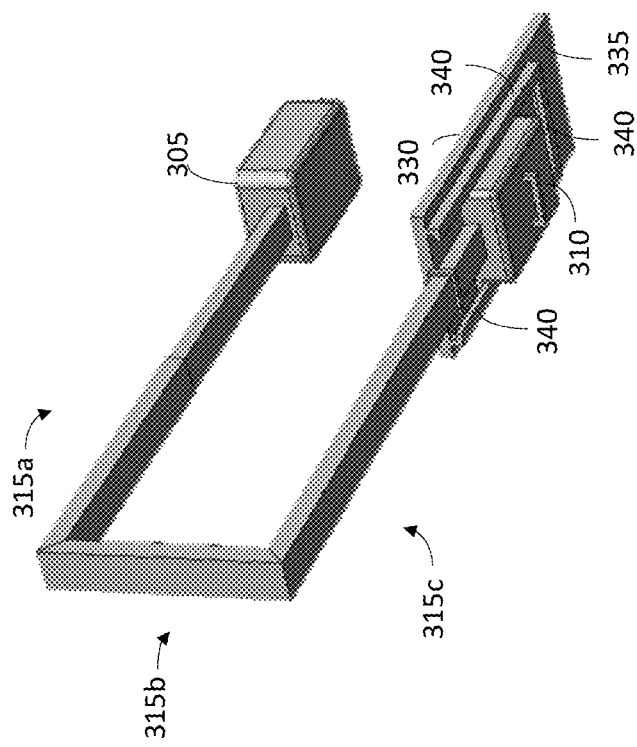

In other embodiments, the x-ray detector 210 may be attachable beneath a surface of the table 230, for example, shown in FIGS. 3E-3H and FIGS. 4C-4E and described below. For example, FIG. 3E illustrates the arm assembly 300 in a first arrangement in which the x-ray detector 310 is opposite of the x-ray source 305. FIG. 3F illustrates the arm assembly 300' in a second arrangement in which the x-ray source 305 and x-ray detector 310 are out of alignment with each other. Attaching the x-ray detector 210 beneath a surface of the table 230 is advantageous in that the x-ray detector 210 is substantially protected from fluids and/or blood during the medical procedure, which would otherwise require cleaning and sterilizing. The table 230 may be made of a material that is substantially radiolucent so that x-rays pass through the table 230 between the x-ray source 205 and the x-ray detector 210. The x-ray source 205 and/or the x-ray detector 210 may be removably attachable to any portion of the table 230 by a joining mechanism to be easily secured, adjusted, and/or removed from the table 230, including by not limited to slides, pins, connectors, magnets, and the like.

Referring now to FIG. 3A, an arm assembly 300 according to another embodiment of the present invention is shown. As for the embodiment shown in FIGS. 3A-3B, an x-ray source 305 and an x-ray detector 310 are coupled to opposite ends 350 of an arm 315. The arm 315 may include a first portion 315*a*, a second portion 315*b*, and a third portion 315*c*. The first portion 315*a* and the third portion 315*c* may be parallel to each other and extend orthogonally from the second portion 315*b*. In an embodiment, the arm 315 includes at least two angles being substantially 90°, generally forming a "C" or "U" shape by the first portion 315*a*, the second portion 315*b*, and the third portion 315*c*. The x-ray source 305 and the x-ray detector 310 may be aligned along an imaging axis 320. For example, FIG. 3A illustrates the arm assembly 300 in a first arrangement in which the x-ray detector 310 is opposite of the x-ray source 305. FIG. 3B illustrates the arm assembly 300' in a second arrangement in which the x-ray source 305 and x-ray detector 310 are out of alignment with each other.

In an embodiment, at least one of the portions 315*a*, 315*b*, 315*c* are retractable. For example, a first part 315*a'* of the first portion 315*a* may be retractable within a second part 315*a''* of the first portion 315*a*. As described above with respect to FIGS. 2A and 2B, the x-ray source 305 may be repositioned relative to the x-ray detector 310. As shown in FIG. 3B, the first part 315*a'* of the first portion 315*a* is retracted within the second part 315*a''* of the first portion 315*a*, so that the retracted arm 315' includes the x-ray source 305 out of alignment with the x-ray detector 310.

A space 325 may be created between the x-ray source 305 and the x-ray detector 310. A patient may be positioned within the space 325 so that an image may be taken. However, when the x-ray source 305 and the x-ray detector 310 are aligned, access to the space 325 may be limited. As described above, the retractable portions 315*a*, 315*b*, and/or 315*c* allow for the x-ray source 305 and/or the x-ray detector 310 to be movable as desired.

In an embodiment, a plurality of the portions 315*a*, 315*b*, 315*c* are retractable, so that the patient may remain stationary. As shown in FIGS. 3C and 3D, both the first portion 315*a* and the third portion 315*c* are retractable. For example, FIG. 3C illustrates the arm assembly 300 in a first arrangement with both the first portion 315*a* and the third portion 315*c* in an extended position. FIG. 3D illustrates the arm assembly 300' in a second arrangement with both the first portion and the third portion in a retracted position. For example, first part 315*a'* of the first portion 315*a* is retractable within the second part 315*a''* of the first portion 315*a*. A first part 315*c'* of the third portion 315*c* is retractable within the second part 315*c''* of the third portion 315*c*. The first part 315*a'*, 315*c'* may be dimensioned smaller than the second part 315*a''*, 315*c''*. The second part 315*a''*, 315*c''* may be hollow in order to receive the first part 315*a'*, 315*c'*.

When the first part 315*a'* is adjusted relative to the second part 315*a''*, the position of the x-ray source 305 relative to the x-ray detector 310 may be altered. Regardless of whether one or both of the x-ray source 305 and the x-ray detector 310 are repositioned relative to each other, they may be brought out of alignment with each other along imaging axis 320 to provide access to the space 325. For example, a patient may be positioned relative to the x-ray detector 310 in the space 325 for imaging prior to a surgical procedure. Once the imaging is complete, the x-ray source 305 may be re-positioned by retracting the first part 315*a'*, 315*c'* of the arm 315 into the second part 315a", 315c". The x-ray detector 310 remains stationary relative to the patient. In an embodiment, the x-ray detector 310 is repositioned while the x-ray source 305 remains stationary relative to the patient. This provides access to the patient in the space 325 by a medical professional, e.g., to conduct the surgical procedure. Upon completion of the procedure, the arm 315 may be adjusted to the original position, e.g., the first part 315a', 315c' is extended out of the second part 315a", 315c".

Figure 3G:
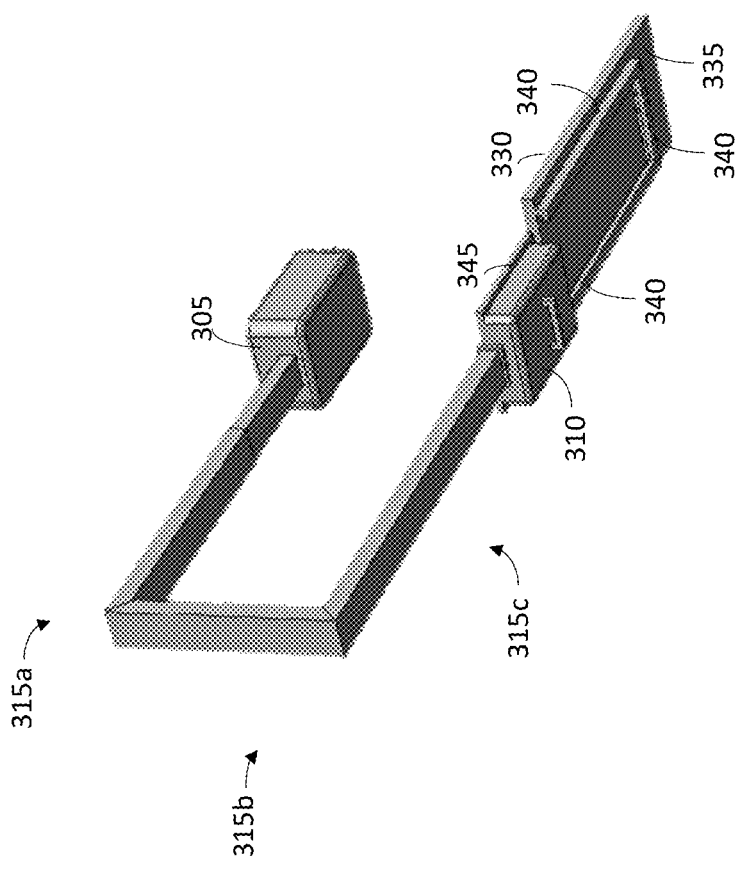

In an embodiment, one of the x-ray source 305 or the x-ray detector 310 may be attachable to a table 330, as shown in FIGS. 3E-3H. In an embodiment, the x-ray detector 310 is attachable to the table 330. The x-ray detector 310 may be attachable to a bottom surface 335 of the table 330. For example, tracks 340 may be configured to receive the x-ray detector 310, so that the x-ray detector 310 is attachable and retainable to the table 330, as shown in FIGS. 3G and 3H. The tracks 340 may be a projection extending from the bottom surface 335 of the table 330, so that a portion 345 of the x-ray detector 310 may be configured to connect to the tracks 340. In an embodiment, the connection may be a tongue and groove and/or a T-shaped slot and projection. For example, FIG. 3G shows a portion 345 of the x-ray detector 310 when the x-ray detector 310 is removed from the table 330. FIG. 3H shows that the portion 345 of the x-ray detector 310 is received in the tracks 340, so that the x-ray detector 310 is attached and retained to the table 330. In an embodiment, the x-ray detector 310 or x-ray source 305 may be attachable to form at least a part of the table surface, for example, shown in FIGS. 2E-2G described below.

Referring now to FIGS. 4A and 4B, another embodiment according to the present invention is shown. FIG. 4A illustrates an arm assembly 400, including an x-ray source 405 coupled at an end 450 of an arm 415, and an x-ray detector 410 coupled at an opposite end 450 of the arm 415. The arm 415 may include a curvature, for example, generally in a "C" shape, so that the x-ray source 405 and the x-ray detector 410 are aligned along an imaging axis 420 when disposed at the ends 450 of the arm 415.

A space 425 may be created between the x-ray source 405 and the x-ray detector 410. A patient may be positioned within the space 425 so that an image may be taken. When the x-ray source 405 and the x-ray detector 410 are aligned, access to the space 425 may be limited. For example, a patient may be positioned in the space 425, but any surgical procedure cannot occur without moving at least one of the patient, the x-ray source 405, and/or the x-ray detector 410.

For the patient to remain stationary, the arm 415 may include a hinge 430 so that the x-ray source 405 and/or the x-ray detector are movable as desired. The hinge 430 may be disposed along the curvature of the arm 415, so that the arm 415 includes a first portion 415a and a second portion 415b. In an embodiment, the hinge 430 may be disposed at a midpoint of the curvature of the arm 415, so that the first portion 415a is equal to the second portion 415b. The hinge 430 allows an x-ray source 405 coupled to a first portion 415a to be hingedly rotated with respect to the x-ray detector 410 coupled to the second portion 415b. In an embodiment, the x-ray detector 410 coupled to the second portion 415b may be hingedly rotated with respect to the x-ray source 405 coupled to the first portion 415a.

In an embodiment, the hinge 430 may be disposed anywhere along the arm 415, e.g., the end 450, so that the x-ray source 405 and/or the x-ray detector 410 are hingedly coupled to the arm 415. For example, see FIGS. 4C-4E. The hinge 430 disposed at an end 450 of the arm 415 allows an x-ray source 405 and/or the x-ray detector 410 to be hingedly rotated with respect to the arm 415 about an axis 435. In an embodiment, the hinge 430 results in the first portion 415a opening with respect to the second portion 415b, although the hinge may be disposed in any alignment to allow one of the first portion 415a and the second portion 415b to be rotated with respect to the other of the first portion 415a and the second portion 415b for accessing the space 425. When the hinge 430 rotates the first portion 415a about the axis 435, the rotated arm 415' alters the position of the x-ray source 405 with respect to the x-ray detector 410, so that the rotated arm 415' includes the x-ray source 405 out of alignment with the x-ray detector 410. Regardless of whether one or both of the x-ray source 405 and the x-ray detector 410 are repositioned relative to each other, they may be brought out of alignment with each other along imaging axis 420 to provide access to the space 425

When the first portion 415a is adjusted relative to the second portion 415b, the position of the x-ray source 405 relative to the x-ray detector 410 is altered. This is advantageous over existing arm assemblies for imaging devices in that one end 450 of the arm 415 may remain stationary while the other end 450 of the arm 415 is repositioned. For example, a patient may be positioned relative to the x-ray detector 410 in the space 425 for imaging prior to a surgical procedure. Once the imaging is complete, the x-ray source 405 may be re-positioned by rotating the first portion 415a of the arm 415 relative to the second portion 415b about the hinge 430. The x-ray detector 410 remains stationary relative to the patient. In an embodiment, the x-ray detector 410 is repositioned while the x-ray source 405 remains stationary relative to the patient. This provides access to the patient in the space 425 by a medical professional, e.g., to conduct the surgical procedure. Upon completion of the procedure, the arm 415 may be adjusted to the original position, e.g., the first portion 415a is rotated back via the hinge 430 relative to the second portion 415b.

Figure 4D:
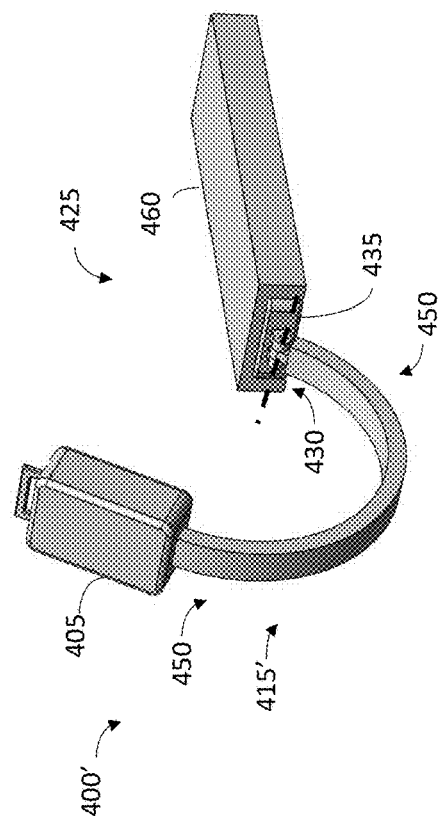
FIGS. 4C-4E illustrate a perspective view of an arm of the medical imaging device according to another embodiment of the present invention.
Figure 4E:
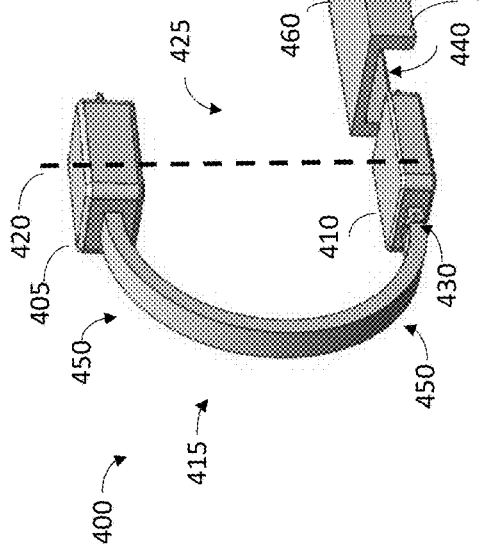
Figure 4C:
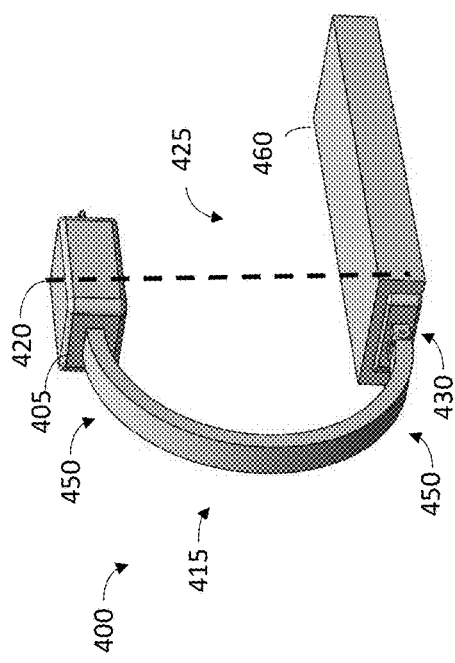

In an embodiment, the hinge 430 may couple the x-ray detector 410 to an end 450 of the arm 415, while the x-ray source 405 is fixedly coupled to the arm 415, as shown in FIGS. 4C-4E. It is also envisioned that in an embodiment the x-ray source 405 may be hingedly coupled to the arm 415 and the x-ray detector 410 is fixedly coupled to the arm 415. The x-ray detector 410 may remain stationary while the x-ray source 405 and the entire arm 415 rotates with respect to the x-ray detector 410.

In an embodiment, the x-ray detector 410 may be attachable to a table 460. For example, the x-ray detector may be slidable along a bottom surface 440. The table may include projections 445 to receive and retain the x-ray detector 410, as described above with respect to FIGS. 3E-3H. In an embodiment, the x-ray detector 410 may form a portion of the table, as shown in FIGS. 2E-2G and described in detail above. The x-ray detector 410 and the x-ray source 405 may be positioned relative to the patient on the table 460, in the space 425.

Referring now to FIGS. 5A and 5B, another embodiment according to the present invention is shown. FIG. 5A illustrates an arm assembly 500, including an x-ray source 505 coupled at an end 540 of an arm 515, and an x-ray detector 510 coupled at an opposite end 540 of the arm 515. The arm 515 may include a curvature, for example, in a general "C" shape, so that the x-ray source 505 and the x-ray detector 510 are aligned along an imaging axis 520 when disposed at the ends 540 of the arm 515.

A space 525 may be created between the x-ray source 505 and the x-ray detector 510 by the alignment of the x-ray source 505 and the x-ray detector 510. A patient may be positioned within the space 525 so that an image may be taken. However, when the x-ray source 505 and the x-ray detector 510 are aligned, access to the space 525 may be limited. A patient may be positioned in the space 525, but a surgical procedure cannot occur without moving at least one of the patient, the x-ray source 505, and/or the x-ray detector 510.

For the patient to remain stationary, the arm 515 may include a pivot point 530 so that the x-ray source 405 and/or the x-ray detector are movable as desired. The pivot point 530 may be disposed along the curvature of the arm 515, so that the arm 515 is divided into a first portion 515a and a second portion 515b. In an embodiment, the pivot point 530 may be disposed at a midpoint of the curvature of the arm 515, so that the first portion 515a is equal in length to the second portion 515b. In an embodiment, the pivot point 530 may be disposed anywhere along the arm 515. The pivot point 530 allows an x-ray source 505 coupled to a first portion 515a to be pivotably rotatable with respect to the x-ray detector 510 coupled to the second portion 515b. In an embodiment, the x-ray detector 510 coupled to the second portion 515b may be pivotably rotatable with respect to the x-ray source 505 coupled to the first portion 515a.

The pivot point 530 may be any mechanical joining of the first portion 515a and the second portion 515b of the arm 515 to be rotatable relative to each other. For example, one of the first or second portions 515a, 515b may include a dowel, or protrusion (not shown) to be received in an aperture of the other of the first or second portion 515a, 515b. The pivot point 530 may allow one of the first or second portion 515a, 515b to rotate in a direction indicated by arrow 535 so that rotated arm 515' includes the x-ray source 505 out of alignment with the x-ray detector 510. For example, the general "C" shape shown in FIG. 5A may become generally an "S" shape shown in FIG. 5B. In an embodiment, one of the first or second portion 515a, 515b may be fully rotatable, 360° around in the direction indicated by arrow 535.

When the first portion 515a is adjusted relative to the second portion 515b, the position of the x-ray source 505 relative to the x-ray detector 510 is altered. This is advantageous over existing arm assemblies for imaging devices in that one end 540 of the arm 515 may remain stationary while the other end 540 of the arm 515 is repositioned. For example, a patient may be positioned relative to the x-ray detector 510 in the space 525 for imaging prior to a surgical procedure. Once the imaging is complete, the x-ray source 505 may be re-positioned by rotating the first portion 515a of the arm 515 relative to the second portion 515b about the pivot point 530. The x-ray detector 510 may remain stationary relative to the patient. In an embodiment, the x-ray detector 510 is repositioned while the x-ray source 505 remains stationary relative to the patient. Regardless of whether one or both of the x-ray source 505 and the x-ray detector 510 are repositioned relative to each other, they may be brought out of alignment with each other along imaging axis 520 to provide access to the space 525. Upon completion of the procedure, the arm 515 may be adjusted to the original position, e.g., the first portion 515a is rotated back relative to the second portion 515b.

Figure 6B:
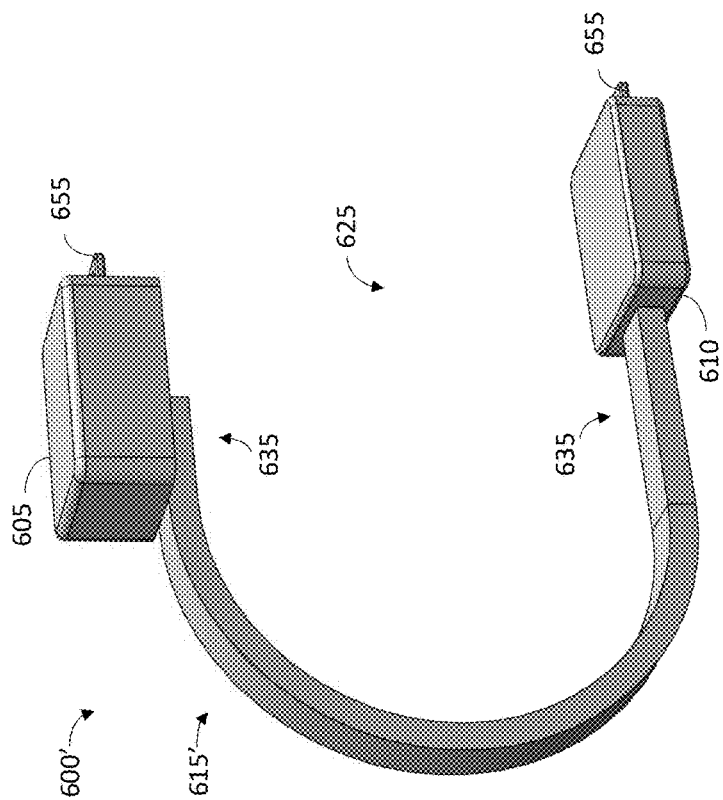
FIGS. 6A-6B illustrate a perspective view of an arm of the medical imaging device according to another embodiment of the present invention.
Figure 6A:
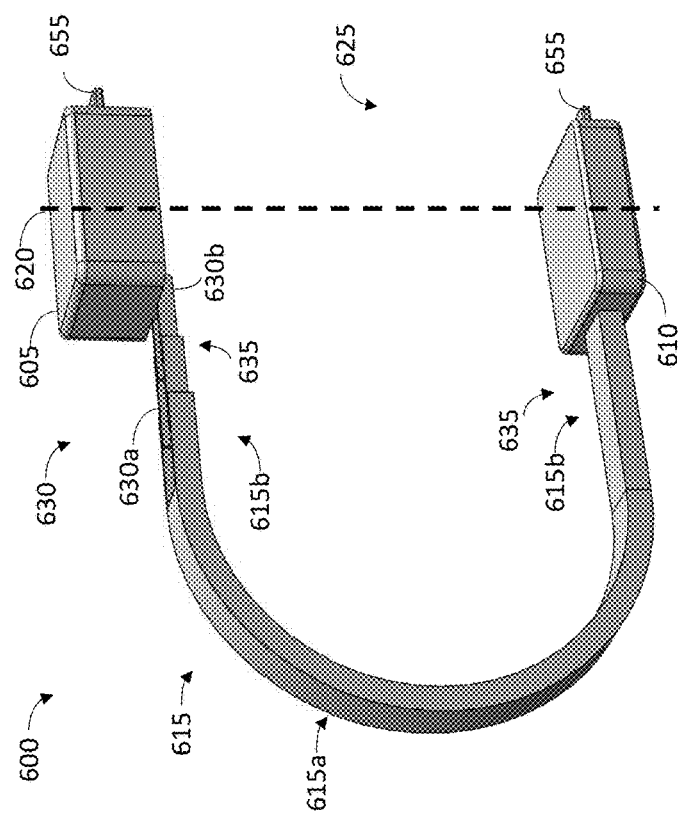

Referring now to FIGS. 6A and 6B, another embodiment according to the present invention is shown. FIG. 6A illustrates an arm assembly 600, including an x-ray source 605 coupled at an end 635 of an arm 615, and an x-ray detector 610 coupled at an opposite end 635 of the arm 615. The arm 615 may include a curvature, for example, in generally a "C" or "U" shape, so that the x-ray source 605 and the x-ray detector 610 are aligned along an imaging axis 620 when disposed at the ends of the arm 615.

A space 625 may be created between the x-ray source 605 and the x-ray detector 610 by the alignment of the x-ray source 605 and the x-ray 610. A patient may be positioned within the space 625 so that an image may be taken. However, when the x-ray source 605 and the x-ray detector 610 are aligned, access to the space 625 may be limited. For example, a patient may be positioned in the space 625, but a surgical procedure cannot occur without moving at least one of the patient, the x-ray source 605, and/or the x-ray detector 610.

For the patient to remain stationary, the arm 615 may include a telescoping portion 630. As shown in FIG. 6A, a telescoping portion 630 may include a plurality of nesting slides 630a, 630b, . . . 630n configured to retract within at least a portion of the arm 615. In an embodiment, the arm 615 may include a telescoping portion at an end 635 of the arm 615, thereby connecting one of the x-ray source 605 and the x-ray detector 610 to the telescoping portion 630. The nesting slides 630a, 630b, . . . 630n may be sized to nest within each other when in a retracted state, and further retracting within the arm 615. For example, at least a portion of the arm 615 may be hollow to receive the nesting slides 630a, 630b, . . . 630n. FIG. 6B shows the arm 615' retracted, so that the nesting slides 630a, 630b, . . . 630n are not visible. When the telescoping portion 630 is retracted, retracted arm 615' includes the x-ray source 605 out of alignment with the x-ray detector 610.

As described above, the arm 615 may include a curvature. In an embodiment, the arm 615 may include a curvature portion 615a and one or more straight portions 615b. The straight portions 615b may be at ends 635 of the arm 615, so that the telescoping portion 630 may extend from the straight portion 615b.

In an embodiment, when the telescoping portion 630 is extended, the x-ray source 605 is aligned with the x-ray detector 610 along imaging axis 620. When the telescoping portion 630 is retracted, e.g., the slides are nested together, the position of the x-ray source 205 relative to the x-ray detector 210 is altered as shown in FIG. 6B. For example, a patient may be positioned relative to the x-ray detector 610 in the space 625 for imaging prior to a surgical procedure. Once the imaging is complete, the x-ray source 605 may be re-positioned by retracting telescoping portion 630 into the arm 615. The x-ray detector 610 remains stationary relative to the patient. In an embodiment, the x-ray detector 610 is repositioned while the x-ray source 605 remains stationary relative to the patient. This provides access to the patient in the space 625 by a medical professional, e.g., to conduct the surgical procedure. Upon completion of the procedure, the arm 615 may be adjusted to the original position, e.g., the telescoping portion 630 is extended so that the x-ray source 605 and the x-ray detector 610 are aligned along the imaging axis 620.

Figure 7B:
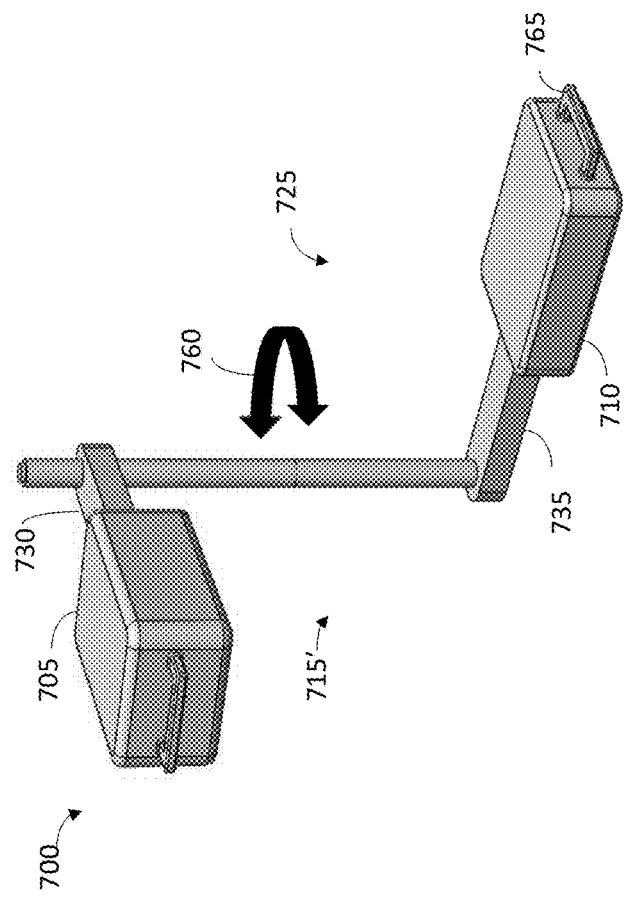
FIGS. 7A-7B illustrate a perspective view of an arm of the medical imaging device according to another embodiment of the present invention.
Figure 7A:
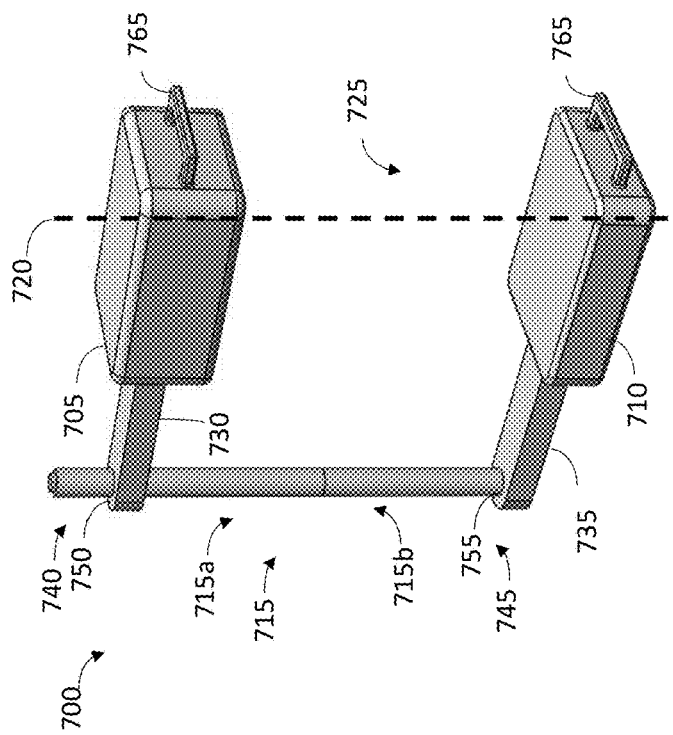

Referring now to FIGS. 7A and 7B, another embodiment according to the present invention is shown. FIG. 7A illustrates an arm assembly 700, including an x-ray source 705 coupled at an end 740, 745 of an arm 715, and an x-ray detector 710 coupled at an opposite end 740,745 of the arm 715. The arm 715 may be a single piece, cylindrical tube. The x-ray source 705 may be rotatably attachable to the arm 715 via a connecting end 730 extending from the x-ray source 705, and the x-ray detector 710 may be rotatably attachable to the arm 715 via a connecting end 735 extending form the x-ray detector 710. In an embodiment, the connecting end 730 of the x-ray source 705 may be rotatably attached to a first end 740 of the arm 715, and the connecting end 735 may be rotatably attached to a second end 745 opposite the first end 740 of the arm 715.

In an embodiment, the connecting ends 730, 735 may be attachable orthogonal to the arm 715, and parallel to each other. For example, the connecting ends 730, 735 may include an aperture 750, 755, respectively, to receive the arm 715. The x-ray source 705 and the x-ray detector 710 may be aligned along an imaging axis 720, so that the arm assembly 700 forms generally a "C" or "U" shape.

A space 725 may be created between the x-ray source 705 and the x-ray detector 710 by the alignment of the x-ray source 705 and the x-ray 710. A patient may be positioned within the space 725 so that an image may be taken. When the x-ray source 705 and the x-ray detector 710 are aligned, access to the space 725 may be limited. For example, a patient may be positioned in the space 725, but a surgical procedure cannot occur without moving at least one of the patient, the x-ray source 705, and/or the x-ray detector 710.

For the patient to remain stationary, the connecting ends 730, 735 may be rotatable about the arm 715, thereby moving the x-ray source 705 and/or the x-ray detector 710 as desired. In an embodiment, the x-ray source 705 may be aligned with the x-ray detector 710 along imaging axis 720 by rotating the connecting ends 730, 735. One of the x-ray source 705 or the x-ray detector 710 may be re-positioned by rotating the connecting end 730, 735 about the arm 715. In an embodiment, the connecting ends 730, 735 may be rotatable in a direction indicated by arrow 760. For example, the general "C" or "U" shape shown in FIG. 7A may become generally an "S" shape shown in FIG. 7B so that rotated arm 715' includes the x-ray source 705 out of alignment with the x-ray detector 710.

A patient may be positioned relative to the x-ray detector 710 in the space 725 for imaging prior to a surgical procedure. Once the imaging is complete, the x-ray source 705 may be re-positioned rotating the x-ray source 705 via the connecting end 730 about the arm 715. The x-ray detector 710 remains stationary relative to the patient and the arm 715. In an embodiment, the x-ray detector 710 is repositioned while the x-ray source 705 remains stationary relative to the patient. This provides access to the patient in the space 725 by a medical professional, e.g., to conduct the surgical procedure. Upon completion of the procedure, x-ray source 705 may be adjusted back to its original position, e.g., the connecting end 730 is rotated about the arm 715 so that the x-ray source 705 and the x-ray detector 710 are aligned along the imaging axis 720.

In an embodiment, the connecting ends 730, 735 may be fixedly attached to the arm 715. The arm 715 may include a first portion 715a and a second portion 715b, rotatable relative to each other. When one of the x-ray source 705 or the x-ray detector 710 is to be moved in order to access the space 725, a first portion 715a of the arm 715 may be rotatable relative to the second portion 715b of the arm 715, so that the x-ray source 705, connecting end 730, and first portion 715a of the arm 715 are rotated in a direction indicated by arrow 760, while the x-ray detector 710, connecting end 735, and second portion 715b of the arm 715 remain stationary. In an embodiment, one of the first or second portions 715a, 715b may be rotatable relative to the other in a direction indicated by arrow 760 in 360°.

Referring now to FIGS. 8A and 8B, another embodiment according to the present invention is shown. FIG. 8A illustrates an arm assembly 800, including an x-ray source 805 coupled at an end 835, 840 of an arm 815, and an x-ray detector 810 coupled at an opposite end 835, 840 of the arm 815. The arm 815 may include a curvature, for example, in a general "C" shape, so that the x-ray source 805 and the x-ray detector 810 are aligned along an imaging axis 820 when disposed at the ends 835, 840 of the arm 815. The x-ray source 805 may be disposed at a first end 835 of the arm 815, and the x-ray detector may be disposed at a second end 840 of the arm 815.

A space 825 may be created between the x-ray source 805 and the x-ray detector 810 by the alignment of the x-ray source 805 and the x-ray 810. A patient may be positioned within the space 825 so that an image may be taken. However, when the x-ray source 805 and the x-ray detector 810 are aligned, access to the space 825 may be limited. For example, a patient may be positioned in the space 825, but a surgical procedure cannot occur without moving at least one of the patient, the x-ray source 805, and/or the x-ray detector 810.

For the patient to remain stationary, at least one of the x-ray source 805 and/or the x-ray detector 810 may be slidable along the arm 815. As shown in FIG. 8B, the x-ray source 805 is adjustable along the curvature of the arm 815. For example, x-ray source 805 is repositioned along a surface 830 of the arm 815. In an embodiment, the x-ray source 805 and/or the x-ray detector 810 may be slidable along an inner surface of the arm 815, although it is envisioned that the x-ray source 805 and/or the x-ray detector 810 may be slidable along an outer surface of the arm 815.

In an embodiment, the x-ray source 805 and/or the x-ray detector 810 may be shaped to match the curvature of the arm 815. For example, a portion 845 of the x-ray source 805 may include a curvature. The curvature may be substantially the same as the curvature of the arm 815. The curvature may be concave or convex, relative to the positioning of the x-ray source 805 and/or the x-ray detector 810. For example, as shown in FIGS. 8A, 8B, the curvature of portion 845 of x-ray source 805 is convex being disposed on an inner surface of the arm 815. It is also envisioned that the x-ray source 805 and/or the x-ray detector 810 may be disposed on an outer surface of the arm 815, such that a curvature of a portion 845 of the x-ray source 805 may be concave.

In an embodiment, the arm 815 may have a track 817, and the x-ray source 805 and/or the x-ray detector 810 may include means for attaching to the track 817 of the arm 815. In an embodiment, the means for attaching may include but not be limited to projections, a tongue and groove configuration, and other joining mechanisms for a slidable attachment. It should also be understood that the x-ray source 805 and/or the x-ray detector 810 may be attached to other areas of the arm 815 as well, including but not limited to a wrap-around sliding mechanism extending from a side 850 of the arm 815 instead of the surface 830 of the arm 815.

When the x-ray source 805 is adjusted relative to the arm 815, the position of the x-ray source 805 relative to the x-ray detector 810 is altered. For example, a patient may be positioned relative to the x-ray detector 810 in the space 825 for imaging prior to a surgical procedure. Once the imaging is complete, the x-ray source 805 may be re-positioned by sliding the x-ray source 805 along the exterior surface 830 of the arm 815. The x-ray detector 810 may remain stationary relative to the patient. In an embodiment, the x-ray detector 810 is repositioned while the x-ray source 805 remains stationary relative to the patient. This provides access to the patient in the space 825 by a medical professional, e.g., to conduct the surgical procedure. Upon completion of the procedure, the x-ray source 805 may be adjusted to the original position, e.g., the x-ray source 805 is extended to the first end 835 of the arm 815 so that the x-ray source 805 is aligned with the x-ray detector 810 along the imaging axis 820.

In the embodiments described with respect to FIGS. 2A-8B, the arm may be made of a material strong enough to maintain stability of the x-ray source and the x-ray detector, but light enough that a user may easily position the arm. For example, the arm may be made of a metal or metal alloy, such as aluminum, or a plastic or composite material.

In the embodiments described with respect to FIGS. 2A-8B, connecting cables (not shown) connecting the x-ray source to the x-ray detector may be disposed within the arm. The arm may be dimensioned so that the hollow area in the second portion may receive excess length of the connecting cable when the first portion is retracted into the second portion. In an embodiment, the connecting cables may be exterior to the arm. The cables may alternatively or additionally be movable to accommodate the rotation of the first portion and/or the second portion. The cables may be movable to accommodate movement of the arm to eliminate pinch points and enhance patient and user safety.

It is also envisioned that counterweights may be needed for the embodiments described with respect to FIGS. 2A-8B, to balance the retracted and/or rotated arm when in a repositioned state, as the center of gravity of the respective arm is shifted.

Figure 9B:
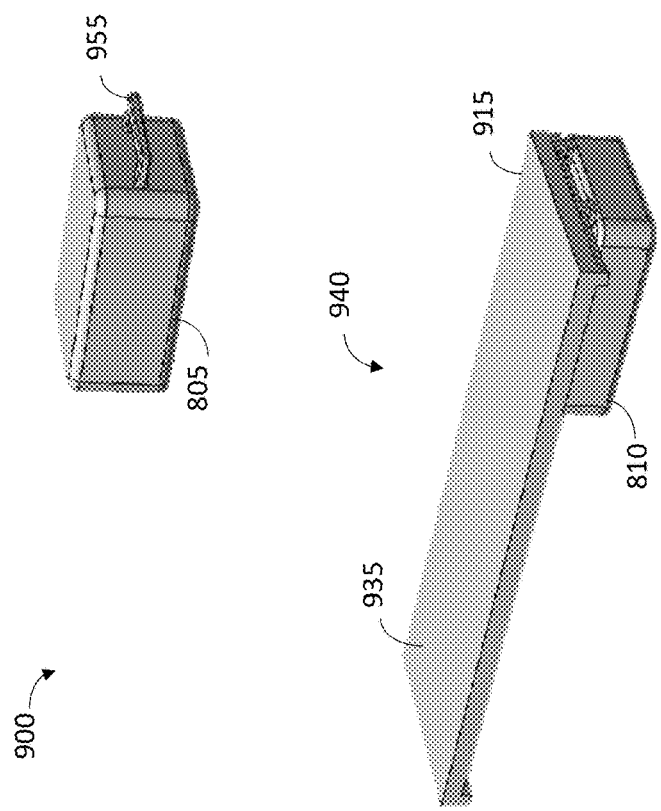
FIGS. 9A-9C illustrate a perspective view of an independent x-ray source and x-ray detector of a medical imaging device according to another embodiment of the invention.
Figure 9A:
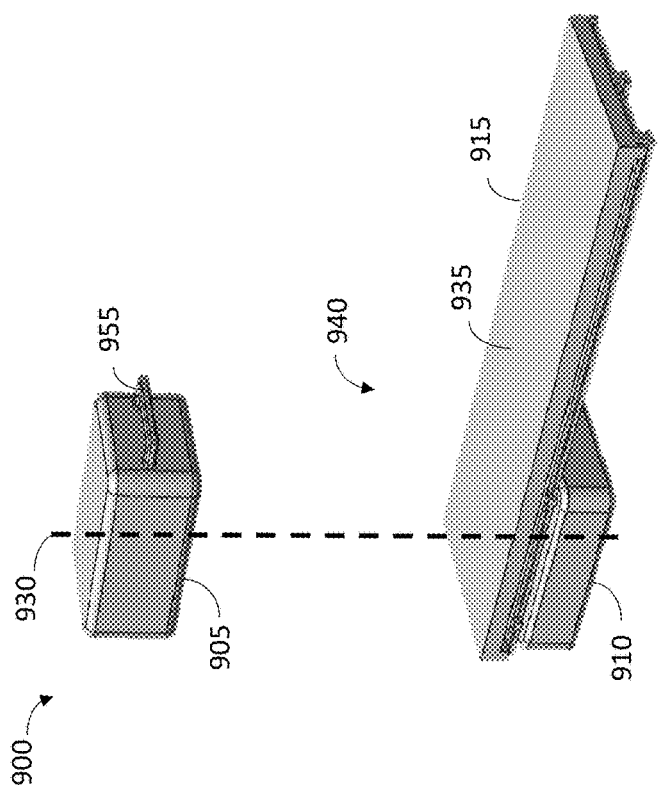
Figure 9C:
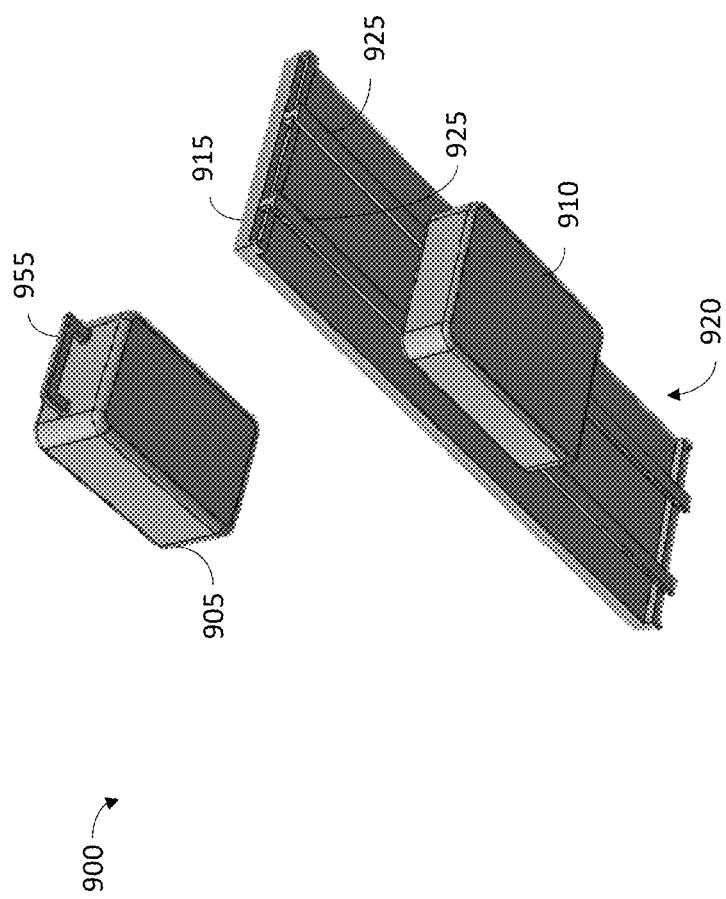

Referring now to FIGS. 9A-9C, an assembly 900 is shown. In the assembly 900, an x-ray source 905 and an x-ray detector 910 may be independent of each other, with no arm connecting each other. One of the x-ray source 905 and the x-ray detector 910 may be coupled to a table 915. Similar to the embodiment described with respect to FIGS. 3E-3H and 4C-4E, one of the x-ray source 905 and the x-ray detector 910 may be slidably attached to a bottom surface 920 of the table 915. Projections 925 may extend from the bottom surface 920 of the table 915, and may be configured to attach and retain the x-ray source 905 or the x-ray detector 910.

In an embodiment, the x-ray source 905 and the x-ray detector 910 may be aligned along an imaging axis 930 for imaging a patient. The patient may be positioned on a top surface 935 of the table 915, in a space 940 created between the x-ray source 905 and the x-ray detector 910. When the imaging is complete, the x-ray source 905 may be re-positioned in an area away from the x-ray detector 910. For example, the x-ray source 905 may be connected to a cable or boom on a ceiling (not shown), which may be raised and/or lowered as desired. In an embodiment, the x-ray source 905 may be removably attachable to other equipment in an operating room. The x-ray detector 910 may be slidable along projections 925 on the bottom surface 920 of the table 915.

When at least one of the x-ray detector 905 and the x-ray detector 910 are re-positioned, medical professionals may access the space 940 to perform surgical procedures on the patient. The patient therefore may remain stationary while the x-ray source 905 and/or the x-ray detector 910 are repositioned. When the surgical procedure is complete, if another image is necessary, the x-ray source 905 and/or the x-ray detector 910 may be positioned back into their original positions, e.g., the x-ray source 905 and the x-ray detector 910 are aligned along imaging axis 930.

In the embodiments described with respect to FIGS. 2A-9C, the imaging device may further include a controller disposed within a cabinet, the controller being operably connected to the arm, x-ray source, and/or the x-ray detector for automatic positioning. The arm may be directly attached to the cabinet, although the arm may optionally also be attached to intermediate assemblies. The controller may send control signals for positioning the x-ray source and the x-ray detector relative to each other. For example, the x-ray source may be directed automatically to the desired position pre-programmed into a memory of the controller. Storing the desired positions in the memory of the controller may also provide greater repeatability and decrease usage time for imaging. A user may, optionally, also enter in the desired position to direct the imaging device components (e.g., the x-ray source, the x-ray detector, arm) via a user interface operably connected to the controller.

The user interface may be means for entering data and operably connected to the controller such as a computer, keyboard, mouse, touchscreen, tablet, mobile phone, and the like. In some embodiments, the user interface may include a microphone and voice activation software controls configured to receive oral commands of the user and position the imaging device as desired. The user interface may additionally include a hands-free operable switch, including but not limited to a foot pedal or switch, operably connected to the controller so that the user may position the components of the imaging device in a hands free manner. The hands-free switch may be independent of the device, so that a user may access the switch e.g., during a surgical procedure. These additional positioning mechanisms are advantageous as the user may desire to adjust the imaging device during a medical procedure when their hands are otherwise occupied with other medical equipment and unable to enter in information by traditional data entry means, thereby saving time and increasing efficiency during the medical procedure.

In an embodiment, when the x-ray source and the x-ray detector are out of alignment with each other, e.g., the x-ray source and the x-ray detector are not aligned along the imaging axis, imaging may be disabled to ensure safety of the user and the patient, minimizing potential radiation exposure. The controller may detect the alignment of the x-ray source and the x-ray detector and disable their operation until properly aligned. As operating rooms and other medical procedure rooms have limited space available, and often multiple people moving about the area, automatically disabling the x-ray source and the x-ray detector may prevent accidentally initializing operation. This may also improve the quality and repeatability of imaging, as imaging will only occur when the x-ray source and the x-ray detector are properly aligned.

It should also be understood that the x-ray source, the x-ray detector, and/or the arm may be manually moved and positioned according to the needs of the patient and/or the user. In some embodiments, the x-ray source and/or the x-ray detector may include a projection, or handle 255, 355, 455, 555, 655, 765, 855, 955. The handle may be coupled to the x-ray source and/or the x-ray detector to provide a point of contact for a user for manual repositioning. While the handle may be disposed at an end of the x-ray source and/or x-ray detector, it should be understood that the handle may be disposed on any side to provide ease of access to the user.

The device may also include sensors S (e.g., radio frequency ID (RFID), global positioning system (GPS), optical laser, infrared, etc.) for verifying an alignment of and/or distance between the x-ray source and the x-ray detector. The x-ray source may not be operable unless the x-ray detector is in alignment along its imaging axis to receive x-rays for imaging, to ensure patient and user safety. Additionally, in some imaging applications such as fluoroscopy, a predetermined source-to-image receptor distance (SID) between the x-ray source and the x-ray detector is required for the imaging device to be operable. Thus, the space between the x-ray source and the x-ray detector is constant when aligned.

It is also envisioned that the imaging devices described in FIGS. 2A-9C may include a mechanical, electro-mechanical, and/or magnetic locking device (depicted, e.g., in FIG. 8 as 819) for locking the x-ray source and/or the x-ray detector in a desired position relative to the device (e.g., arm, operating table). The locking device 819 ensures the x-ray source and the x-ray detector remain immobile during an imaging process and/or when adjusted for a surgical procedure to ensure patient and user safety. The user may engage and/or disengage the locking device 819 when manually positioning the imaging device. Optionally, the locking device 819 may engage automatically when positioning one of the x-ray source, x-ray detector, and arm to a pre-determined position. It should also be understood that the locking device 819 may automatically engage and/or disengage during automatic movement of the imaging device, for example, by the controller. A kill switch, or emergency shut-off may also be provided so that automatic movement of the device may be halted by the user to ensure patient and user safety. The locking device 819 and/or kill switch may be able to engage and/or disengage remotely, and in a hands-free manner (e.g., foot pedal, voice-activation) when the user may be performing a medical procedure.

Figure 10:
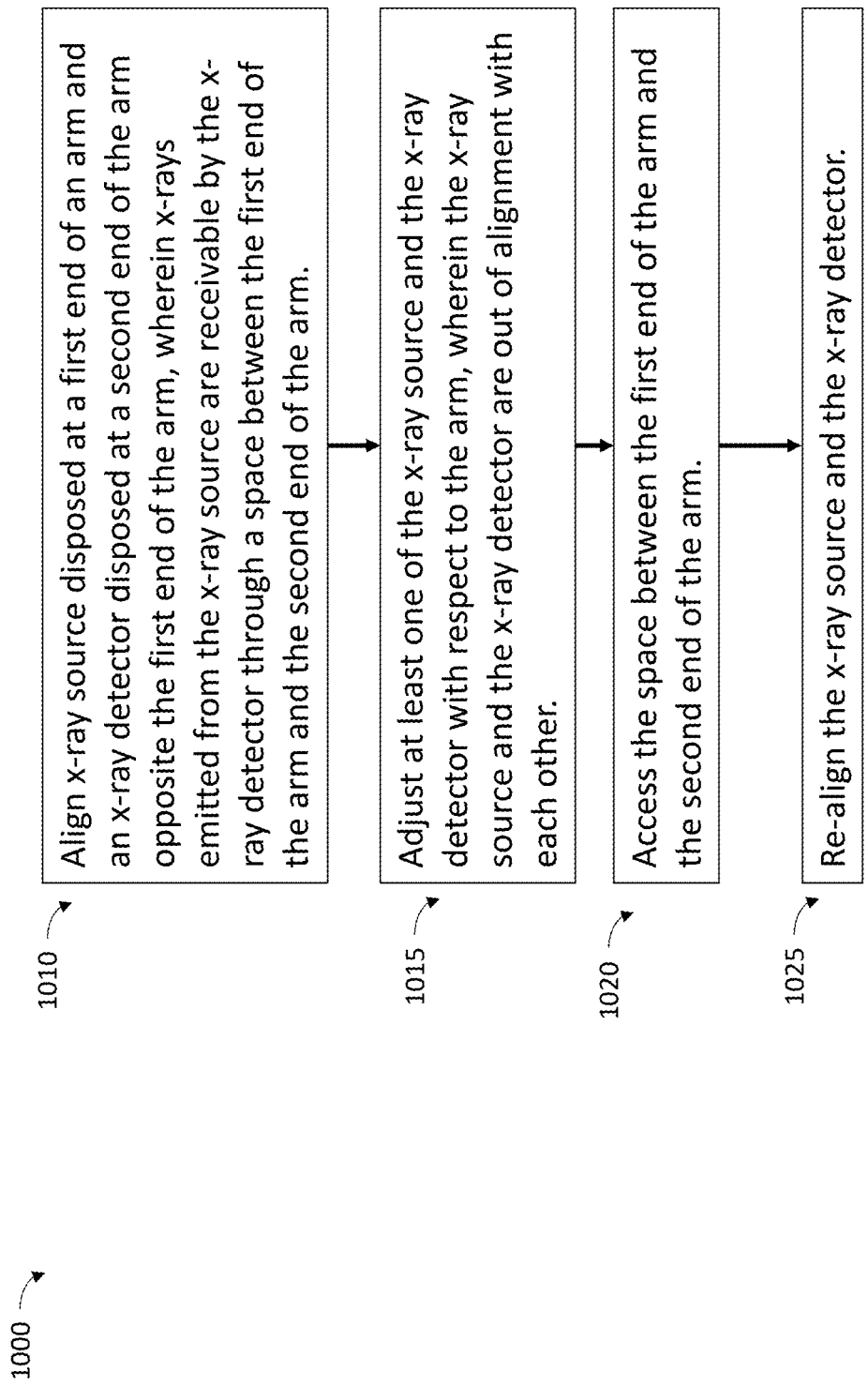
FIG. 10 illustrates a flow diagram of a method of operating a medical imaging device according to an embodiment of the present invention.

Referring now to FIG. 10, a flow diagram 1000 illustrating a method according to the present invention is shown. At step 1010, an x-ray source disposed at a first end of an arm is aligned with an x-ray detector disposed at a second end of the arm opposite the first end of the arm. The x-ray source emits x-rays which are receivable by the x-ray detector through a space between the first end of the arm and the second end of the arm. A patient may be positioned in the space between the first end of the arm and the second end of the arm, so that the x-ray image captures the desired bone and tissue images.

At step 1015, at least one of the x-ray source and the x-ray detector are adjusted with respect to the arm. Adjusting the at least one of the x-ray source and the x-ray detector results in the x-ray source and the x-ray detector being out of alignment with each other. At step 1020, the space between the first end of the arm and the second end of the arm is accessed. As described above, a surgical procedure may be performed on a patient in the area that was imaged. When the surgical procedure is complete, at step 1025, the x-ray source and the x-ray detector may be re-aligned with each other, so that another image may be taken. As described above, a follow-up image after completion of a surgical procedure may verify correct bone settings and/or placement of implants.

While the embodiments described herein pertain to fluoroscopic imaging devices, the inventions relate to any medical imaging device for extremity imaging in which an imaging source is spaced apart from and facing an imaging receptor. An example of such an arrangement include x-ray devices including a C-arm. For example, the inventions herein can also be applied to any x-ray medical imaging device, such as 2D x-ray technology, tomosynthesis, computed tomography, and/or combinations thereof. Examples of such systems include U.S. Pat. Nos. 7,123,684; 7,577, 282; 7,831,296; 8,175,219; 8,565,374; and 8,787,522, and U.S. Patent Application Publication No. 2016/0256125, which are incorporated by reference herein.

Some embodiments of the disclosed device may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A medical imaging device, comprising:
   an arm including a first end, a second end, and an arc-shaped curvature between the first end of the arm and the second end of the arm,
   wherein the arm includes a track having a termination at the first end of the arm;
   an x-ray detector fixed to the second end of the arm; and
   an x-ray source slidably coupled to the track, wherein the track limits a sliding range of the x-ray source along the arc-shaped curvature from a first position proximate the x-ray detector to a second position located a maximum distance along the arc-shaped curvature away from the x-ray detector, wherein the second position is defined by the termination of the track at the first end of the arm, wherein when the x-ray source is positioned at the second position at the first end of the arm, the x-ray source and the x-ray detector are aligned along an imaging axis, and wherein when the x-ray source is aligned with the x-ray detector, the x-ray source is configured to be at a predetermined constant source-to-image receptor distance (SID) from the x-ray detector.

2. The medical imaging device of claim 1, wherein the x-ray source is coupled to the track by one of interlocking projections and a tongue and groove configuration.

3. The medical imaging device of claim 1, wherein the track is attached to an inner surface of the arm.

4. The medical imaging device of claim 1, further comprising a controller associated with the x-ray source, the controller configured to automatically position the x-ray source along the length of the track.

5. The medical imaging device of claim 4, wherein the controller is configured to automatically position the x-ray source to a pre-programmed position along the length of the track.

6. The medical imaging device of claim 4, further comprising a user-interface, wherein the controller is operatively connected to the user-interface to enable a user to enter a desired position of the x-ray source along the length of the track, the user interface being selected from one of a computer, a keyboard, a mouse, a touchscreen, a tablet, a mobile phone, a foot pedal, and voice-assisted controls including a microphone and voice activation software controls configured to receive oral commands from the user to position the x-ray source along the length of the track.

7. The medical imaging device of claim 1, wherein the x-ray source includes at least one handle for manually moving the x-ray source along the length of the track.

8. The medical imaging device of claim 1, further comprising sensors arranged and configured to detect a position of the x-ray source relative to the x-ray detector.

9. The medical imaging device of claim 1, further comprising a locking device to secure a position of the x-ray source along the length of the track.

10. The medical imaging device of claim 9, wherein the locking device is selected from one of a mechanical, an electro-mechanical, and a magnetic locking device.

11. The medical imaging device of claim 9, wherein the locking device is manually moveable between an engaged position and a disengaged position.

12. The medical imaging device of claim 9, wherein the locking device is automatically engageable during a movement of the x-ray source.

13. A medical imaging device, comprising:
an arm including a first end, a second end, an arc-shaped curvature between the first end of the arm and the second end of the arm, and a track extending along at least a portion of the arc-shaped curvature of the arm and terminating at the first end;
an x-ray detector fixed to the second end of the arm;
an x-ray source slidably coupled along a length of the track so that when the x-ray source is positioned at a maximum distance away from the x-ray detector and at the first end of the arm, the x-ray source and the x-ray detector are aligned along an imaging axis, and when aligned the x-ray source is configured to be at a predetermined constant source-to-image receptor distance (SID) from the x-ray detector, and wherein the x-ray source being slidable to a position away from the first end of the arm and toward the x-ray detector; and a controller associated with the x-ray source, the controller configured to automatically position the x-ray source along the length of the track.

14. The medical imaging device of claim 13, wherein the x-ray source is coupled to the track by one of interlocking projections and a tongue and groove configuration.

15. The medical imaging device of claim 13, wherein the controller is configured to automatically position the x-ray source to a pre-programmed position along the length of the track.

16. The medical imaging device of claim 13, further comprising a user-interface, wherein the controller is operatively connected to the user-interface to enable a user to enter a desired position of the x-ray source along the length of the track, the user interface being selected from one of a computer, a keyboard, a mouse, a touchscreen, a tablet, a mobile phone, a foot pedal, and voice-assisted controls including a microphone and voice activation software controls configured to receive oral commands from the user to position the x-ray source along the length of the track.

17. The medical imaging device of claim 13, further comprising a locking device to secure a position of the x-ray source along the length of the track.

18. A medical imaging device, comprising:
an arm including a first end, a second end, and an arc-shaped curvature between the first end of the arm and the second end of the arm, and
wherein the arm includes a track having a termination at the first end of the arm;
an x-ray detector fixed to the second end of the arm;
an x-ray source slidably coupled to the track,
wherein the track limits a sliding range of the x-ray source along the arc-shaped curvature from a first position proximate the x-ray detector to a second position located a maximum distance along the arc-shaped curvature away from the x-ray detector,
wherein the second position is defined by the termination of the track at the first end of the arm,
wherein when the x-ray source is positioned at the first end of the arm, the x-ray source and the x-ray detector are aligned along an imaging axis, and when aligned the x-ray source is configured to be at a predetermined constant source-to-image receptor distance (SID) from the x-ray detector; and
sensors arranged and configured to detect a position of the x-ray source relative to the x-ray detector.

19. A method of manufacturing a medical imaging device, the method comprising:
providing an arm including a first end, a second end, and an arc-shaped curvature between the first end of the arm and the second end of the arm;
coupling a track to the arm, the track extending along at least a portion of the arc-shaped curvature of the arm and terminating at the first end;
coupling an x-ray detector at the second end of the arm; and
coupling an x-ray source to the track so that, in use, the x-ray source is slidably coupled along a length of the track so that when the x-ray source is positioned at a maximum distance away from the x-ray detector at the first end of the arm, the x-ray source and the x-ray detector are aligned along an imaging axis and when aligned the x-ray source is configured to be at a predetermined constant source-to-image receptor distance (SID) from the x-ray detector, and so that the x-ray source is positionable away from the first end of the arm and toward the x-ray detector.

20. The method of manufacturing a medical imaging device of claim 19, wherein the x-ray source is coupled to the track by one of interlocking projections and a tongue and groove configuration.

* * * * *